US007854935B2

(12) United States Patent
Li et al.

(10) Patent No.: US 7,854,935 B2
(45) Date of Patent: Dec. 21, 2010

(54) HERBAL THERAPY FOR THE TREATMENT OF ASTHMA

(75) Inventors: Xiu-Min Li, Mamaroneck, NY (US); Hugh A. Sampson, Larchmont, NY (US); Ming-Chun Weng, Weifang (CN)

(73) Assignee: Herbal Spring, LLC, Larchmont, NY (US)

( * ) Notice: Subject to any disclaimer, the term of this patent is extended or adjusted under 35 U.S.C. 154(b) by 0 days.

(21) Appl. No.: 10/592,912

(22) PCT Filed: Mar. 14, 2005

(86) PCT No.: PCT/US2005/008600
§ 371 (c)(1),
(2), (4) Date: Dec. 14, 2007

(87) PCT Pub. No.: WO2005/092361
PCT Pub. Date: Oct. 6, 2005

(65) Prior Publication Data
US 2008/0213298 A1 Sep. 4, 2008

Related U.S. Application Data

(60) Provisional application No. 60/554,607, filed on Mar. 19, 2004.

(51) Int. Cl.
*A61K 36/06* (2006.01)
*A61K 9/00* (2006.01)
*A61K 47/00* (2006.01)
*A61K 36/00* (2006.01)
(52) U.S. Cl. .................. 424/195.15; 424/439; 424/400; 424/725
(58) Field of Classification Search ........................ None
See application file for complete search history.

(56) References Cited

U.S. PATENT DOCUMENTS

| | | | |
|---|---|---|---|
| 6,503,542 B2 | 1/2003 | Sheu | |
| 6,630,176 B2 | 10/2003 | Li et al. | |
| 6,686,502 B1 | 2/2004 | Cai et al. | |
| 6,696,440 B1 | 2/2004 | Bridges et al. | |
| 6,869,621 B2 * | 3/2005 | Hwang et al. | 424/725 |
| 2003/0130200 A1 * | 7/2003 | Houck et al. | 514/17 |
| 2004/0103908 A1 * | 6/2004 | Prakash et al. | 131/359 |

FOREIGN PATENT DOCUMENTS

JP 2000-0044481 A 2/2000

OTHER PUBLICATIONS

DW ACC 2002/217632, Dec. 2001, Derwent CN, Liu.*
European Search Report, App. No. EP 05 72 5636, Int'l Pub. No. PCT/US2005/008600, date of mailing Jul. 2, 2009.
International Search Report, PCT/US2005/008600, date of mailing Sep. 16, 2005.
Written Opinion, PCT/US2005/008600, date of mailing Sep. 16, 2005.
Li et al., "The Chinese herbal medicine formula MSSM-002 suppresses allergic airway hyperreactivity and modulates TH1/TH2 responses in a murine model of allergic asthma," *Journal of Allergy and Clinical Immunology* 6(4):660-668 (2000).
Szelenyi et al., "Herbal remedies for asthma treatment: between myth and reality," *Drugs of Today / Medicamentos de Actualidad* 38(4):273-274 (2002).
Lin et al., "Dimerization of the N-terminal amphipathic alpha-helix domain of the fungal immunomodulatory protein from Ganoderma tsugae (Fip-gts) defined by a yeast two-hybrid system and site-directed mutagenesis," *Journal of Biological Chemistry* 272(32):20044-20048 (1997).
Bielory et al., "Herbal interventions in asthma and allergy," *Journal of Asthma* 36(1):1-65 (1999).
Li et al, "Induction of pulmonary allergic responses by antigen-specific Th2 cells," Journal of Immunology 160(3):1378-1384 (1998).
But et al., "Chinese Herbal Medicine in the Treatment of Asthma and Allergies," *Clinical Reviews in Allergy and Immunology* (1996), vol. 14, pp. 253-269.
Hsieh "Evaluation of efficacy of traditional Chinese medicines in the treatment of childhood bronchial asthma: clinical trial, immunological tests and animal study," *Pediatric Allergy and Immunology* (1996), vol. 7, pp. 130-140.
Ziment et al., "Alternative medicine for allergy and asthma," *Current Reviews of Allergy and Clinical Immunology* (Oct. 2000), vol. 106, No. 4, pp. 603-614.
Egashira et al., "A Multicenter Clinical Trial of TJ-96 in Patients with Steroid-Dependent Bronchial Asthma A Comparison of Groups Allocated by the Envelope Method," *Ann NY Acad Sci* (1993) 685:580-583.
Lee et al., "Butterbur, a herbal remedy, attenuates adenosine monophosphate induced nasal responsiveness in seasonal allergic rhinitis," *Clin Exp Allergy* (2004) 34:110-114.
Li et al., "103 cases of postpartum uroschesis treated by acupuncture at huiyang point," *J Tradit Chin Med* (1996)16(3):198-200.
Toda et al., "Effect of an Herbal Preparation, Saiboku-to (TJ-96), on Antigen-Induced Airway Hyperresponsiveness and Eosinophil Infiltration in Actively Sensitized Guinea Pigs," *Ann NY Acad Sci* (1993) 685:561-571.
Zhang et al., "Clinical Study on Jianfei Pill in Preventing and Treating Recurrence of Infantile Asthma," *Chinese Journal of Integrated Traditional and Western Medicine* (1997) 17(4):204-206.

* cited by examiner

*Primary Examiner*—Christopher R Tate
*Assistant Examiner*—Randall Winston
(74) *Attorney, Agent, or Firm*—Brenda Herschbach Jarrell; Emilie Porter Huck; Choate, Hall & Stewart LLP

(57) ABSTRACT

The present invention provides herbal formulas, and compositions thereof, that can treat or reduce the severity, intensity, or duration of asthma and asthma-related symptoms. The compositions may optionally include one or more adjuvants, cytokines, encapsulating materials, or pharmaceutically acceptable carriers or excipients, and may be administered prior to, during, or after the development of asthmatic symptoms in a patient in need thereof.

13 Claims, 39 Drawing Sheets

Fig. 5 Three-dimensional HPLC pattern of Ku-Shen

Fig. 6 The HPLC fingerprint of Ku-Shen at 254nm

Fig.7 Three-dimensional HPLC pattern of Gan-Cao

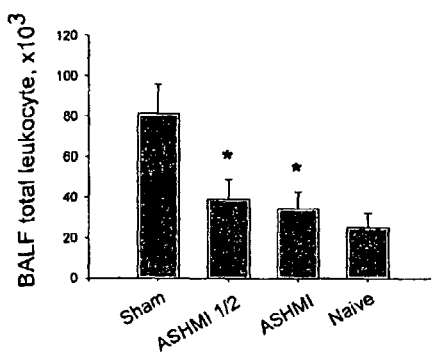
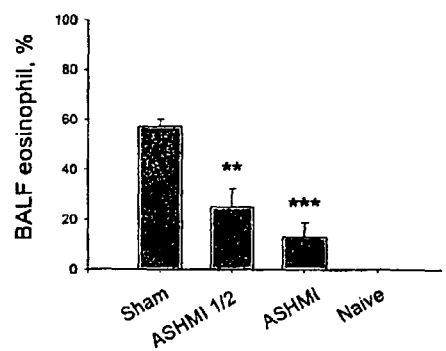
Fig 12. ASHMI reduced Ag-induced pulmonary inflammation: Total number of cells and differential counts of BALF cells were determined by microscopic evaluation. A. shows the total number of cells and B. shows percent of eosinophils. Data are Mean ± SEM of 6-8 mice from each group. *, $p<0.05$; , $p<0.01$ vs sham and *, $p<0.001$.
FIGURE 12

Fig4. Lung histology. Mice in each group (n=4/group) were necropsied after airway response measurement and unlavaged left upper lobe lungs were fixed in neutral buffered formaldehyde. Five-μm paraffin sections were stained with periodic acid-Schiff's reagent (PAS) for goblet cells. A. shows goblet cell hyperplasia in airway from a saline placebo treated mouse. B. illustrates markedly reduced mucus goblet cells in airways of ASHMI treated mice. C. shows absence of goblet cells in airways of naïve mice.

FIGURE 13

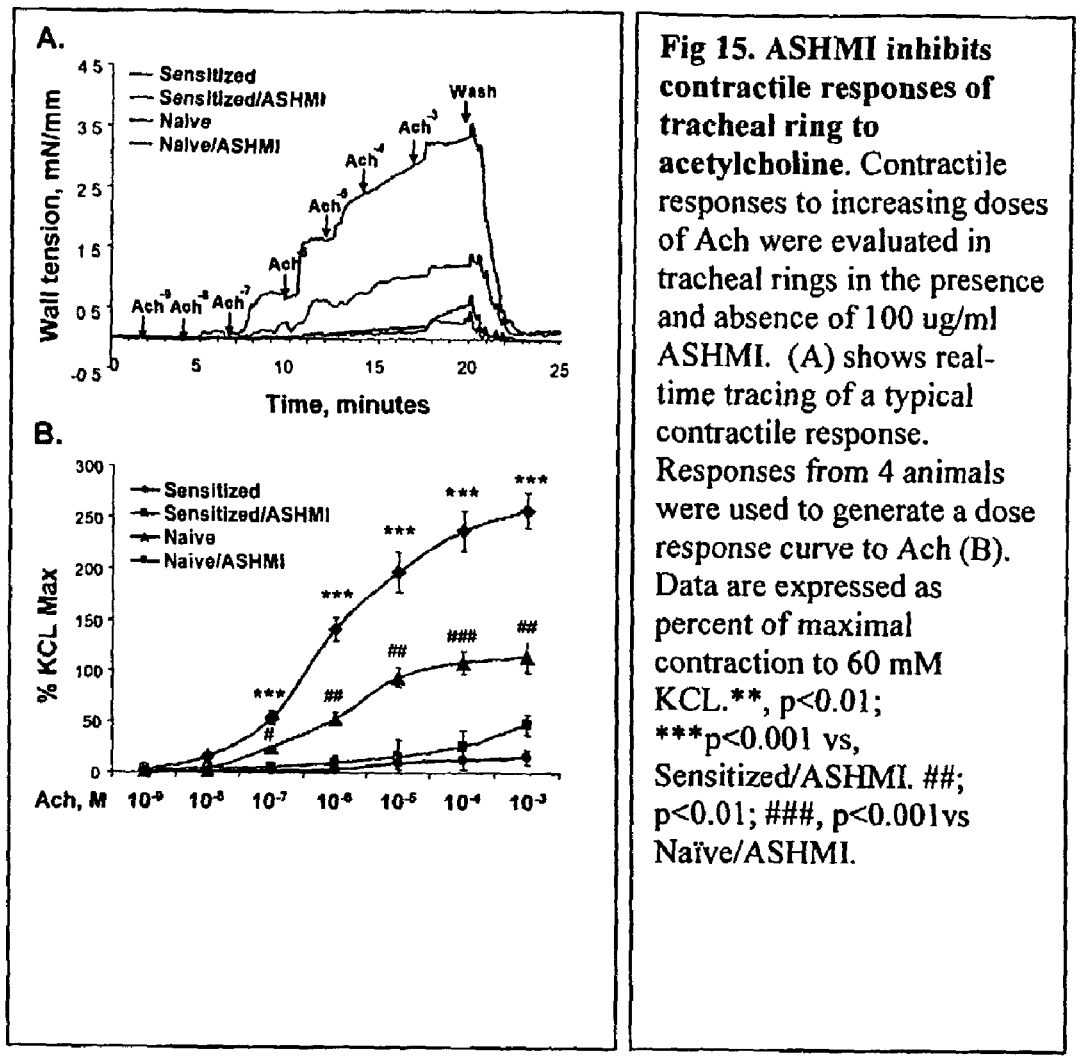

Fig 15. ASHMI inhibits contractile responses of tracheal ring to acetylcholine. Contractile responses to increasing doses of Ach were evaluated in tracheal rings in the presence and absence of 100 ug/ml ASHMI. (A) shows real-time tracing of a typical contractile response. Responses from 4 animals were used to generate a dose response curve to Ach (B). Data are expressed as percent of maximal contraction to 60 mM KCL., $p<0.01$; *$p<0.001$ vs, Sensitized/ASHMI. ##; $p<0.01$; ###, $p<0.001$ vs Naïve/ASHMI.

FIGURE 15

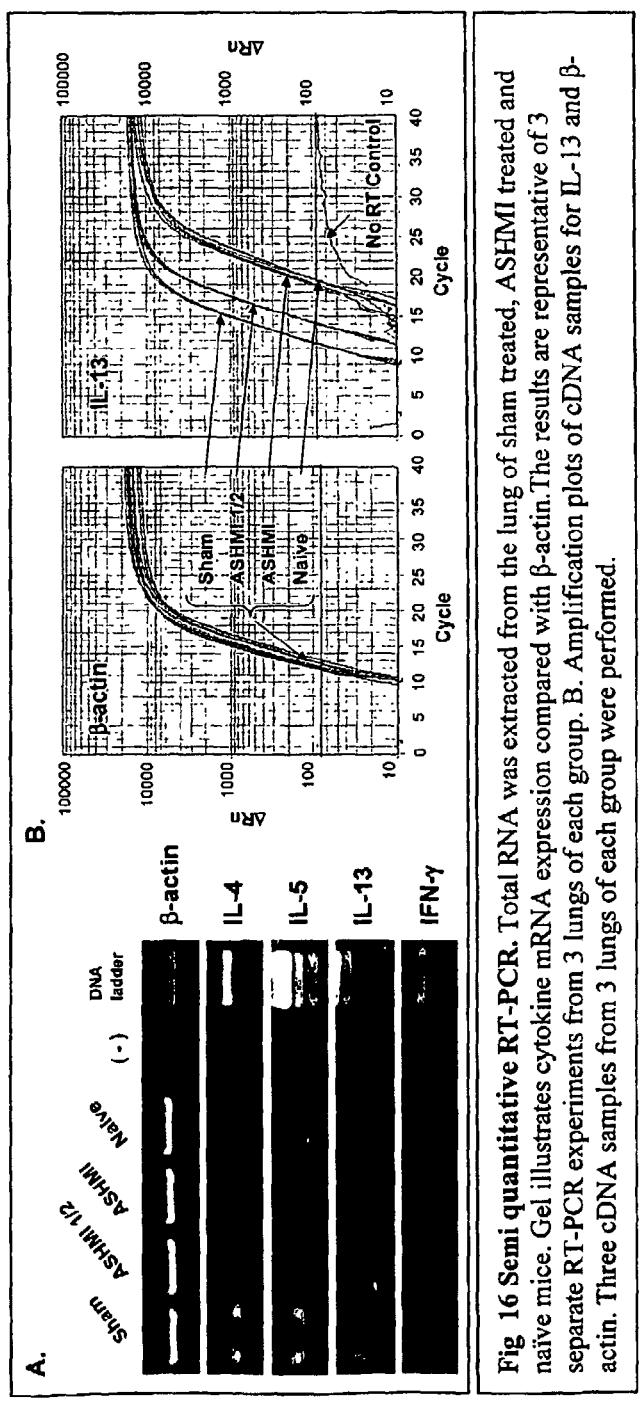

Fig. 16 Semi quantitative RT-PCR. Total RNA was extracted from the lung of sham treated, ASHMI treated and naïve mice. Gel illustrates cytokine mRNA expression compared with β-actin. The results are representative of 3 separate RT-PCR experiments from 3 lungs of each group. B. Amplification plots of cDNA samples for IL-13 and β-actin. Three cDNA samples from 3 lungs of each group were performed.

FIGURE 16

Fig 17. Flow cytometry: Data show the percent of CD4+CD44+ IL-4+ cells.

Fig 19. Effect of ASHMI on D10 cells. D10 cells were cultured in the presence of CA and irradiated syngeneic splenocytes in the presence or absence of ASHMI at 50µg/ml. Supernatants were collected 72-hrs later, and cytokine levels were determined by ELISA. Results are expressed as mean ± SEM of triplicate cultures from three experiments. *$p<0.05$; ***$p<0.001$ vs CA.

Fig 20. Phenotype of Th2 polarized cell line, D10.G4.1. Flow cytometry results show D10 cells phenotype $CD44^{high}CD62L^{neg}CCR7^{neg}$ (the open histogram).

Fig 21. Western blot for determining GATA-3 protein expression in lung tissue (A) and D10 cells (B).

Fig 22. ChIP Assay. Illustration of ChIP assay using a ChIP Assay Kit (Upstate Biotechnology. Lake Placid NY) indicates GATA-3 binding to IL-4 promoter and enhancer in the D10 cells with or without CA-stimulation in the presence or absence of ASHMI treated cells.

HERBAL THERAPY FOR THE TREATMENT OF ASTHMA

CROSS REFERENCE TO RELATED APPLICATIONS

This application claims the benefit under 35 U.S.C. §371 of International Application No.: PCT/US2005/008600, published as WO 2005/092361 A1, filed Mar. 14, 2005, which claims priority to U.S. provisional patent application 60/554, 607, filed Mar. 19, 2004; the entire contents of each of which are hereby incorporated herein by reference.

This application claims priority to U.S. Provisional Application No. 60/554,607, filed on 19 Mar. 2004, the entirety of which is hereby incorporated herein by reference.

FIELD OF THE INVENTION

The present invention relates generally to an herbal formulation. More particularly, the invention is directed to an herbal formulation consisting of a mixture of Chinese herbs useful for treating or lessening the severity of asthma.

BACKGROUND OF THE INVENTION

Asthma is a major public health problem in the United States. Nearly 17 million Americans suffer from this often debilitating disease. Moreover, asthma morbidity and mortality have been rising over the last two decades. The prevalence rate of asthma increased by 75% from 1980 to 1994. And, despite the increased use of medications, the rate of asthma-related deaths rose 58% and now exceeds 180,000 annually. While the reasons for increased asthma morbidity and mortality remain unknown, it is hoped that improved approaches to asthma therapy will reverse this trend. See Redd S C. Asthma in the United States: burden and current theories. *Environ Health Perspect* 2002; 110 Suppl 4:557-560; and Kay A B. Asthma and inflammation. *J. Allergy Clin. Immunol.* 1991; 87:893-910.

Allergic asthma is characterized by airway hyper-responsiveness (AHR), airway inflammation, and elevated IgE. See Kay A B., Asthma and inflammation. *J. Allergy Clin. Immunol.* 1991; 87:893-910. This results in symptomatic effects including, but not limited to, episodic breathlessness, wheezing, chest tightness, and coughing. See Lemanske R F J, A review of the current guidelines for allergic rhinitis and asthma. *J. Allergy Clin. Immunol.* 1998; 101:S392-S396. Furthermore, the airways of asthmatic subjects are characterized by chronic inflammation with infiltration of the bronchial mucosa by lymphocytes, eosinophils and mast cells as well as epithelial desquamation, goblet cell hyperplasia, and thickening of the submucosa (airway remodeling). See Kay A B., Asthma and inflammation. *J.Allergy Clin.Immunol.* 1991; 87:893-910; McFadden E R J, Gilbert Iowa., Asthma. *N Engl J Med* 1992; 327:1928-1937; Beasley R, Roche W R, Roberts J A, Holgate S T, Cellular events in the bronchi in mild asthma and after bronchial provocation. *Am.Rev.Respir.Dis.* 1989; 139:806-817.

Human atopic subjects, when exposed to the relevant antigen (Ag), exhibit an acute IgE-dependent response, often followed by a late-phase inflammatory response (LPR) hours later. The immediate response is triggered by mast cell degranulation and release of mediators, such as histamine, tryptase, leukotrienes, and platelet-activating factor (PAF). LPR is associated with infiltration of inflammatory cells, predominantly eosinophils, which release eosinophil major basic protein, leukotrienes, and other mediators that damage the airway epithelium and induce bronchoconstriction. See Metzger W J, Huuiinghake G W, Richerson H B. Late asthmatic responses: inquiry into mechanisms and significance. *Clin.Rev.Allergy* 1985; 3:145-165; Busse W W, Vrtis R F, Dick E C. The role of viral infections in intrinsic asthma: activation of neutrophil inflammation. *Agents Actions Suppl.* 1989; 28:41-56; Lemanske R F, Kaliner M A. Late-phase allergic reactions. In: Middleton Jr, Reed C E, Ellis E F, Adkinson N F, Yunginger J W, eds. *In Allergy: Principles and Practice*. St. Louis: C. V. Mosby, Co., 1993: 320; Pauwels R. The relationship between airway inflammation and bronchial hyperresponsiveness. *Clin.Exp.Allergy* 1989; 19:395-398; Drazen J M, Arm J P, Austen K F. Sorting out the cytokines of asthma. *J.Exp.Med.* 1996; 183:1-5.

Numerous studies demonstrated that the Th2 cytokines, IL-4, IL-5 and IL-13 play a central role in the pathogenesis of asthma. For example, IL-4 and IL-13 induce B cell switching to IgE synthesis. This process favors Th2 cell differentiation, mast cell development, eosinophil and basophil activation, and airway remodeling including new collagen, goblet cell formation, and airway smooth muscle (ASM) hypertrophy. See Ware L B, Matthay M A. Keratinocyte and hepatocyte growth factors in the lung: roles in lung development, inflammation, and repair. *Am J Physiol Lung Cell Mol Physiol* 2002; 282:L924-L940. IL-4 and IL-13 can also increase ASM contraction perhaps by desensitizing β2 AR in ASM. IL-5 is responsible for eosinophil differentiation, maturation, and activation.

A major driving force behind chronic asthma is the long-lived memory Th2 cells that secrete Th2 cytokines following antigen encounter. These memory Th2 cells often arise early in life and persist following repeated encounters with allergen. Thus, targeting memory Th2 cells offers a therapeutic approach for asthma.

A Th2 transcription factor that is critical to Th2 cytokine memory is GATA-3, whose activation of Th2 cytokine gene expression is through chromatin remodeling. Therefore, immunomodulation of GATA-3 is important in down-regulating all critical Th2 cytokine production (IL-4, IL-5 and IL-13).

Because inflammation is a principal factor in AHR, attention has focused on reducing inflammatory processes. Corticosteroids, the most potent nonspecific anti-inflammatory agents, produce substantial improvement in objective lung functions of asthmatics and are still the cornerstone of asthma treatment. See Leonard P, Sur S. Asthma: future directions. *Med Clin North Am* 2002; 86:1131-1156. Corticosteroids, however, do not significantly improve airway remodeling, do not inhibit the release of mast cell mediators, have no direct bronchodilator activity, and at the same time, induce significant systemic adverse effects when given for prolonged periods. See Jain V V, Kitagaki K, Busing a T, Hussain I, George C, O'shaughnessy P, Kline J N. CpG-oligodeoxynucleotides inhibit airway remodeling in a muline model of chronic asthma. *J Allergy Clin Immunol* 2002; 110:867-872; and National Heart LaBI. Guidelines for the diagnosis and management of asthma. National Heart, Lung, and Blood Institute. National Asthma Education Program. Expert Panel Report. *J Allergy Clin Immunol* 1991; 88:425-534.

Although inhaled corticosteroids greatly reduce the side effects, systemic side effects of inhaled corticosteroids (ICS) also have been reported. Adrenal suppression, decreased bone metabolism, and decreased growth are a concern in children taking ICS. See WHO Study Group on Global Strategy for Asthma Management and Prevention. Anonymous-Global strategy for asthma management and prevention. Bethesda, Md.: *National Institutes of Health,* 1995:95-3659;

and Akinbami L J, Schoendorf K C. Trends in childhood asthma: prevalence, health care utilization, and mortality. *Pediatrics* 2002; 110:315-322. Corticosteroids also produce overall immune suppression, which results in increased susceptibility to infections. In addition, recent studies indicate that continuous daily treatment with ICS had no long-term therapeutic benefit in terms of lung function because although anti-inflammatory therapy reduced the incidence of asthma symptoms in subjects with persistent asthma, it did not alter progressive lung changes or prevent recurrence of symptoms shortly after discontinuation of therapy. The Childhood Asthma Management Program Research Group. Long-term effects of Budesonide or nedocromil in children with asthma. *N Engl J Med* 2000; 343:1054-1063. Additionally, two new classes of recently introduced asthma medications, leukotriene inhibitors and anti-IgE, have shown only marginal benefits.

In view of this, there remains an unmet need to develop alternative, safe, and effective asthma treatments. Although a role for complementary and alternative medicine (CAM) in asthma treatment is uncertain because of the lack of well controlled scientific studies, the use of CAM in Western countries has grown substantially over the last 10 years. See Steurer-Stey C, Russi E W, Steurer J. Complementary and alternative medicine in asthma: do they work? *Swiss Med Wkly* 2002; 132:338-344; MacLennan A H, Wilson D H, Taylor A W. Prevalence and cost of alternative medicine in Australia. *Lancet* 1996; 347:569-573; Kessler R C, Davis R B, Foster D F, Van Rompay M I, Walters E E, Wilkey S A, Kaptchuk T J, Eisenberg D M. Long-term trends in the use of complementary and alternative medical therapies in the United States. *Ann Intern Med* 2001; 135:262-268; and Eisenberg D M, Kessler R C, Foster C, Norlock F E, Calkins D R, Delbanco T L. Unconventional medicine in the United States. Prevalence, costs, and patterns of use. *N Engl J Med* 1993; 328:246-252. One recent study found that up to 50% of asthmatics were using some form of CAM, and that a growing number of asthma patients wish to use some form of CAM.

Traditional Chinese Medicine (TCM), including the use of Chinese herbal medications (CHM), is one of the oldest medical practices in the world and has benefited patients for thousands of years. For example, the symptoms of asthma such as coughing, wheezing and chest tightness were described in the book Yellow Emperor's Inner Classic, which is thought to have been compiled in the first or second century C.E., by which time the theoretical foundations of TCM were in place. In addition to acupuncture, the most widely used TCM treatments are "herbal formulas" comprised of specific mixtures of several components. The combination of herbs is believed to produce synergistic effects and reduce possible side effects. Previous studies support this notion, indicating that some herbal formulas are more effective than their individual components. For example, the widely used anti-allergy formula TJ-19 (Traditional Chinese-Japanese herbal medicine) is known to more effectively inhibit histamine induced reactions than any of its individual herbal components. See Hosoya E, Yamamura Y. Recent advances in the pharmacology of kampo (Japanese herbal) medicines. Tokyo: *Excerpta Medica*, 1998:260.

Accordingly, the development of a TCM treatment for asthma comprising a manageable number of herbal ingredients is a desirable and unmet need. Additionally, the development of a TCM targeting Th2 transcription factor is also a desirable and unmet need.

SUMMARY OF THE INVENTION

The present invention encompasses the finding that a combination of three herbs, and active components thereof, are useful for the treatment of asthma. Thus, the present invention relates to an herbal formula for the treatment of asthma, wherein said formula consists of the three herbs Ling-Zhi, Ku-Shen, and Gan-Cao. In particular, the present invention provides methods of treating or lessening the severity of asthma and/or asthma-related symptoms in a patient in need thereof comprising the step of administering to said patient an herbal formula of the present invention.

In certain embodiments of the present invention, said formula further comprises a pharmaceutically acceptable carrier, adjuvant, or vehicle.

In other embodiments of the present invention, said formula is administered in combination with one or more additional therapeutic agents. For example, the herbal formulas of the present invention may be administered in combination with corticosteroids (e.g., inhaled, injected, or orally delivered corticosteroids), bronchodilators, etc. used to treat asthmatic symptoms.

According to another aspect of the present invention, the herbal composition of the present invention may optionally be characterized in one or more animal model systems.

According to yet another embodiment, the present invention provides methods for identifying active components of the present herbal formula.

Definitions

As used herein, the following definitions shall apply unless otherwise indicated.

"Active component": An "active component" of an herb, herbal formulation, or preparation, is a compound or collection of compounds that is present in the herb, herbal formulation, or preparation and that, when separated from at least some other herbal components, retains at least some of a desired biological activity of the intact herb, herbal formulation, or preparation. In certain embodiments, the active component retains at least about 20% of the biological activity, or, alternatively, at least about 30%, 40%, 50%, 60%, 70%, 80%, 90%, 95%, or 99%.

"Allergen": An "allergen" is an antigen that (i) elicits an IgE response in an individual; (ii) elicits an asthmatic reaction (e.g., chronic airway inflammation characterized by eosinophilia, airway hyperresponsiveness, and excess mucus production), whether or not such a reaction includes a detectable IgE response; and/or (iii) elicits an allergic reaction (e.g., sneezing, watery eyes, puritis, diarrhea, anaphylaxis), whether or not such a reaction includes a detectable IgE response.

"Allergic individual": "Allergic individual" refers to an individual with sensitivities to particular antigens or allergens as exhibited by (i) eliciting an IgE response in an individual sufficient to cause a measurable clinical response; (ii) eliciting an asthmatic reaction (e.g., chronic airway inflammation characterized by eosinophilia, airway hyperresponsiveness, and excess mucus production), whether or not such a reaction includes a detectable IgE response; and/or (iii) eliciting the signs and symptoms of an allergic reaction (e.g., sneezing, watery eyes, puritis, redness, diarrhea, anaphylaxis), whether or not such a reaction includes a detectable IgE response.

Such an individual has a reaction to a relatively innocuous antigen that does not cause a similar reaction upon exposure in most other members of the population. This reaction in an allergic individual can cause a harmful immune response and/or tissue damage. Symptoms of allergy may consist of exaggerated or pathological reaction (e.g., sneezing, respiratory distress, itching, or skin rashes) to substances, situations, or physical states that are without comparable effect on the average individual.

"Allergic reaction": An allergic reaction is a clinical response by an individual to an antigen. Symptoms of allergic reactions can affect the cutaneous (e.g., urticaria, angioedema, pruritus), respiratory (e.g., wheezing, coughing, laryngeal edema, rhinorrhea, watery/itching eyes), gastrointestinal (e.g., vomiting, abdominal pain, diarrhea), and/or cardiovascular (if a systemic reaction occurs) systems. For the purposes of the present invention, an asthmatic reaction is considered to be a form of allergic reaction. In certain embodiments, the allergic reaction involves an IgE response in an individual sufficient to cause a measurable clinical response.

"Animal": The term animal, as used herein, refers to non-human animals, including, for example, mammals, birds, reptiles, amphibians, and fish. In certain embodiments, the non-human animal is a mammal (e.g., a rodent, a mouse, a rat, a rabbit, a monkey, a dog, a cat, or a pig). An animal may be a transgenic animal.

"Antigen": An "antigen" is (i) any compound or composition that elicits an immune response; and/or (ii) any compound that binds to a T cell receptor (e.g., when presented by an MHC molecule) or to an antibody produced by a B cell. Those of ordinary skill in the art will appreciate that an antigen may be a collection of different chemical compounds (e.g., a crude extract or preparation) or a single compound (e.g., a protein).

"ASHMI": The term "ASHMI", as used herein, refers to the three herb formula of the present invention as described in the Examples section.

"Associated with": When two entities are "associated with" one another as described herein, they are linked by a direct or indirect covalent or non covalent interaction. In certain embodiments, the association is covalent. Desirable non covalent interactions include hydrogen bonding, van der Waals interactions, hydrophobic interactions, magnetic interactions, electrostatic interactions, etc. Also, two entities or agents may be "associated" with one another by being present together in the same composition.

"Asthmatic individual": The term "asthmatic individual" refers to an individual who experiences asthmatic symptoms (e.g., chronic airway inflammation characterized by eosinophilia, airway hyperresponsiveness, and excess mucus production) upon inhalation of, or other contact with, a particular substance or antigen. Asthmatic individuals do not necessarily exhibit a detectable production of IgE.

"Cytokine": A "cytokine" is a small molecule that is released from or expressed by a cell and can alter the behavior or regulate the activity of one or more immunologically relevant target cells expressing a receptor for the cytokine. Cytokines that, if expressed by an antigen presenting cell, or by another cell, during presentation of antigen to a T cell would induce a particular response in that T cell can be classified according to the type of response they induce in the T cell. For example, cytokines that induce a Th1 response (e.g., IL-12, IL-2, IL-18, IL-1β or fragments thereof, IFNα, and/or IFNγ, etc.) are referred to herein as "Th1 stimulating cytokines"; cytokines that induce a Th2 response (e.g., IL-4, etc.) are referred to herein as "Th2 stimulating cytokines." Cytokines that are produced during a Th1 response (e.g., IFNγ, TNFβ, etc.) are referred to as "Th1 cytokines"; cytokines that are produced during a Th2 response (e.g., IL-4, IL-5, etc.) are referred to as "Th2 cytokines."

"Effective amount": The "effective amount" of an agent or composition refers to the amount necessary to elicit the desired biological response. The effective amount of the active components of an herb or herbal remedy is the amount necessary to decrease a particular sign and/or symptom (e.g., rhinorrhea, watery eyes, puritis, drop in blood pressure, drop in body temperature, level of IgE, production of cytokines, etc.) of an allergic reaction or asthma. The decrease may be a 10%, 20%, 30%, 40%, 50%, 60%, 70%, 80%, 90%, 95%, or 98% decrease. The effective amount of an active component of an herb or herbal remedy in a tolerizing composition is the amount that, when administered to an individual who is sensitized to an antigen, results in tolerization of the individual to the antigen.

"Herb": An "herb" according to the present invention includes any portion of the plant in which active components are found. For example, active components may be found one or more portions of a plant including in the leaves, flowers, stems, roots, seeds, spores, stalks, rhizomes, fruit, or fruiting bodies of said plant.

"Inducing agents": Inducing agents are compounds or other agents that induce a professional antigen presenting cell (pAPC) to produce stimulating cytokines. For example, if it is desired that a pAPC secrete Th1 stimulating cytokines, then factors such as LPS, CD40, CD40 ligand, BCGs, oligonucleotides containing CpG motifs, TNFα, and microbial extracts such as preparations of Staphylococcus aureus, heat killed Listeria, etc. can act as inducing agents ("Th1 inducing agents"). If instead it is desired that a pAPC secrete Th2 stimulating cytokines, then other factors (e.g., factors that induce IL-4 expression or inhibit IL-12 expression) can act as inducing agents ("Th2 inducing agents"). It will be appreciated by those of ordinary skill in the art that an inducing agent is usually an adjuvant.

"Isolated": As will be clear from context, the term "isolated" means (i) separated from at least one of the components with which the isolated entity or compound is associated in nature; and/or (ii) produced by a non-natural process (e.g., synthesized in vitro or produced by a recombinant organism).

"Mast cell": As will be apparent from context, the term "mast cell" is often used herein to refer to one or more of mast cells, basophils, and other cells with IgE receptors.

"Patient": According to the present invention, a "patient" means an animal, a mammal, and/or a human.

"Peptide": According to the present invention, a "peptide" comprises a string of at least three amino acids linked together by peptide bonds. The term "peptide" may refer to an individual peptide or a collection of peptides. For the purposes of the present invention, peptides may contain only natural amino acids. Alternatively, non natural amino acids (i.e., compounds that do not occur in nature but that can be incorporated into a polypeptide chain; see, for example, http://www.cco.caltech.edu/~dadgrp/Unnatstruct.gif, which displays structures of non-natural amino acids that have been successfully incorporated into functional ion channels) and/or amino acid analogs, as are known in the art, may be employed. Also, one or more of the amino acids in a "peptide" may be modified, for example, by the addition of a chemical entity such as a carbohydrate group, a phosphate group, a farnesyl group, an isofamesyl group, a fatty acid group, a linker for conjugation, functionalization, or other modification, etc.

"Placebo": The term "placebo" (and related term "sham"), as used herein, refers to an inactive substance or preparation used as a control in an experiment or test to determine the effectiveness of an herbal formula of the present invention.

"Polynucleotide" or "oligonucleotide": The terms "polynucleotide" and "oligonucleotide" refer to polymers of nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyladenosine, 5-methylcytidine, C5 bromouridine, C5 fluorouridine, C5 iodouridine, C5 propynyl uridine, C5 propynyl cytidine, C5 methylcytidine, 7 deazaadenosine, 7 deazaguanosine, 8 oxoadenosine, 8 oxoguanosine, O(6) methylguanine, and 2-thiocytidine), chemically modified bases, biologically modified bases (e.g., methylated bases), intercalated bases, modified sugars (e.g., 2'-fluororibose, ribose, 2'-deoxyribose, and hexose), and/or modified phosphate groups (e.g., phosphorothioates and 5' N phosphoramidite linkages).

"Purified": A compound is "purified" in accordance with the present invention if it is separated from substantially all other components. In certain embodiments, a purified compound is at least about 75% pure, or, alternatively, it is at least about 80%, 90%, 95%, 97%, 98%, or 99% pure.

"Sensitized individual": A "sensitized" individual is a human or animal who has been exposed to a given antigen and has mounted an immune response to that antigen that results in the display of one or more allergic or asthmatic symptoms when the individual is exposed to the antigen.

"Sensitized mast cell": A "sensitized" mast cell is a mast cell that has surface bound antigen-specific IgE molecules. The term is necessarily antigen specific. That is, at any given time, a particular mast cell will be "sensitized" to certain antigens (those that are recognized by the IgE on its surface) but will not be sensitized to other antigens.

"Sham": As used herein, the term "sham: is interchangeable with the term placebo. The term "sham" (and related term "placebo"), as used herein, refers to an inactive substance or preparation used as a control in an experiment or test to determine the effectiveness of an herbal formula of the present invention.

"Th1 response" and "Th2 response": Th1 and Th2 responses are well-established alternative immune system responses that are characterized by the production of different collections of cytokines and/or cofactors. For example, Th1 responses are generally associated with the production of cytokines such as IL-1$\beta$, IL-2, IL-12, IL-18, IFN$\alpha$, IFN$\gamma$, TNF$\beta$, etc.; Th2 responses are generally associated with the production of cytokines such as IL-4, IL-5, IL-10, etc. The extent of T cell subset suppression or stimulation may be determined by any available means including, for example, intra-cytoplasmic cytokine determination. In certain embodiments of the invention, Th2 suppression is assayed, for example, by quantitation of IL-4, IL-5, and/or IL-13 in stimulated T cell culture supernatant or assessment of T cell intra-cytoplasmic (e.g., by protein staining or analysis of mRNA) IL-4, IL-5, and/or IL-13; Th1 stimulation is assayed, for example, by quantization of IFN$\alpha$, IFN$\gamma$, IL-2, IL-12, and/or IL-18 in activated T cell culture supernatant or assessment of intra-cytoplasmic levels of these cytokines.

BRIEF DESCRIPTION OF THE DRAWINGS

FIG. 12 shows the reduction of Ag-induced pulmonary inflammation due to ASHMI treatment.

FIG. 13 depicts the lung histology from ASHMI treated mice as compared to placebo-treated mice.

FIG. 15 shows the effect of ASHMI on contractile responses of tracheal rings to acetylcholine.

FIG. 16 shows the comparison of cytokine mRNA expression between mice treated with a full dose of ASHMI, those treated with a half dose of ASHMI, those treated with placebo and naïve mice.

DETAILED DESCRIPTION OF CERTAIN EMBODIMENTS OF THE INVENTION

Figure 1:
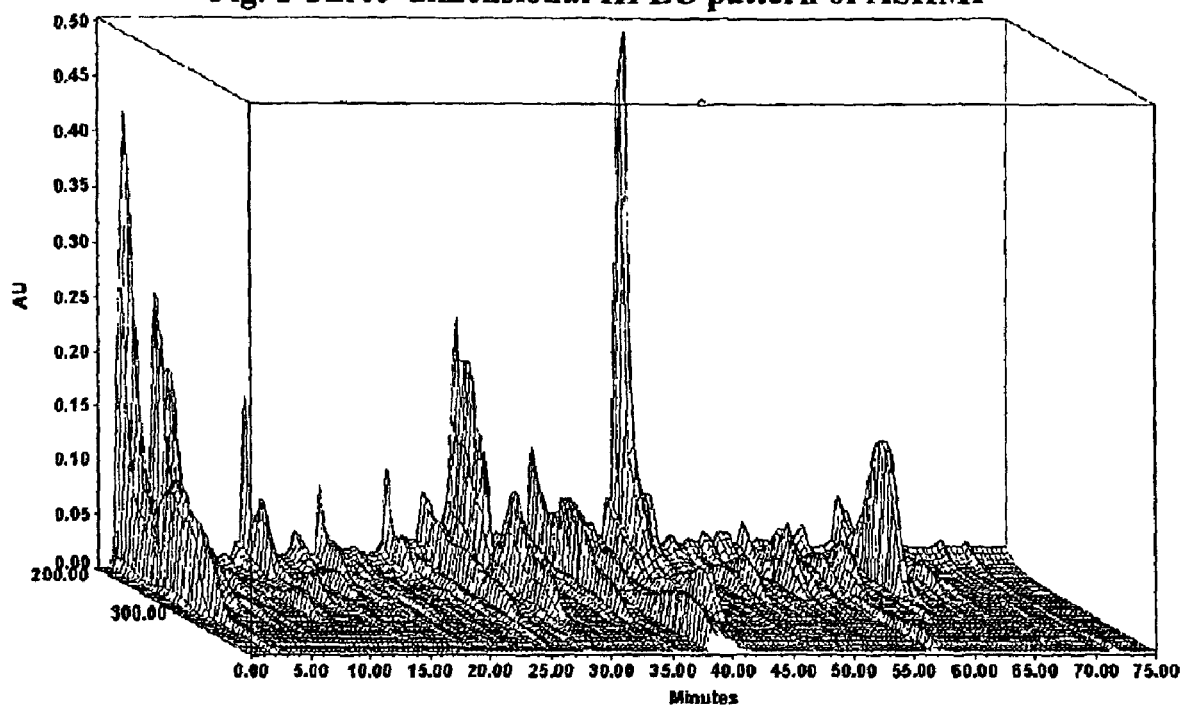
FIG. 1 depicts the three-dimensional HPLC pattern of ASHMI as obtained by Reverse-Phase HPLC using diode array detection.

The present invention unites insights from traditional Chinese medicine and modern Western medicine to formulate treatments for asthma. Traditional Chinese medicine ("TCM") employs herbal formulations to treat bodily ailments. In some cases, single herbs or herb derivatives are used. More commonly, however, "formulas" or specific combinations of several particular herbs are administered. The recipes for these formulas are assembled into books known as "formularies". The original formulary, Discussion of Cold-Induced Disorders and Miscellaneous Diseases (Shang Han Za Bing Lun), was written at the end of the second century A.D. by Zhang Zhong-Jing. This book was later edited by Wang Shu-He, who divided it into two parts, Discussion of Cold-Induced Disorders (Shang Han Lun), which deals with externally-contracted diseases, and Essentials from the Golden Cabinet (Jin Gui Yao Lue), which is primarily concerned with internally-generated disorders (Bensky et al., Chinese Herbal Medicine Formulas & Strategies. Eastland Press, 1999; incorporated herein by reference). These two books contain 374 formulas.

It has been reported that some anti-asthma TCM formulas improved symptoms and medical scores, increased PEF values, and/or reduced the need for steroids and β2-agonists in patients, and reduced airway hyperreactivity and eosinophilia in animal models of asthma. A recent study found that Butterbur, a Chinese herbal medicine, produced a significant steroid-sparing effect. See Lee D C K, Haggart K, Robb F M, Lipworth B J. Butterbur, a herbal remedy, confers complementary anti-inflammatory activity in asthmatic patients receiving inhaled corticosteroids. *Clin & Exp Allergy* 2004; 34:110-114. This study and others provide some scientific evidence supporting the use of TCM formulas and herbal derivatives for the treatment of asthma and allergy. For example, MSSM-002 is an anti-asthma TCM which contains 14 herbs. However, the standardization of such a combination of herbs, to ensure the quality, potency, and consistency, is a prohibitive undertaking. See Bielory L, Lupoli K. Herbal interventions in asthma and allergy. *J.Asthma* 1999; 36:1-65; Lee D C K, Haggart K, Robb F M, Lipworth B J. Butterbur, a herbal remedy, confers complementary anti-inflammatory activity in asthmatic patients receiving inhaled corticosteroids. *Clin & Exp Allergy* 2004; 34:110-114; and Ziment I, Tashkin D P. Alternative medicine for allergy and asthma. *J Allergy Clin Immunol* 2000; 106:603-614.

The present invention provides a new herbal formula for the treatment of asthma according to Western principles. Specifically, the formulas of the present invention, and pharmaceutically acceptable compositions thereof, contain only 3 herbs and/or extracts thereof, thereby making herbal quality control easier.

The present invention relates to an herbal formula for the treatment of asthma, wherein said herbal formula consists of the three herbs Ling-Zhi, Ku-Shen, and Gan-Cao. While not wishing to be bound by theory, we found that the herbal formula of the present invention has immunoregulatory effects on memory Th2 cells, and suppresses GATA-3 expression and activation of memory Th2 cells. Thus, the herbal formula of the present invention has an immunotherapeutic effect in asthma treatment. Accordingly, another embodiment of the present invention relates to a method of suppressing GATA-3 expression and activation of memory Th2 cells by administering to a patient an herbal formula of the present invention.

The present invention provides an herbal formula that reduces one or more asthmatic symptoms and signs including but not limited to airway hyperresponsiveness, bronchoconstriction, difficulty breathing, vasodilation, decrease in blood pressure, increased IgE levels, increased numbers of goblet cells, increased Th2 cytokine levels, bronchial inflammation, anaphylaxis, and death.

According to certain embodiments, the herbal formula of the present invention demonstrates a reduction in symptoms that is at least as significant as that observed with known therapeutic agents such as corticosteroids. According to other embodiments, the reduction in symptoms occurs more quickly than is seen with known therapeutic agents (e.g., conventional antigen immunotherapy and/or steroid treatment), is more persistent than that observed with known therapeutic agents, and/or is more extensive than that achieved by known therapeutic agents.

Herbs for use in the herbal formula of the present invention will generally be provided in their natural, herbal form. The herbs may be harvested from any location at any time of the year. According to certain embodiments, the herbal formulas have the active components at concentrations sufficient to treat asthmatic symptoms. According to other embodiments, the herbs are harvested in a manner which maximizes the efficacy of the herbal composition.

The herbs for the formulas of the present invention may be selected based on any number of criteria including, but not limited to, appearance (e.g., color, texture, etc.), smell, feel, HPLC "finger printing", chromatographic (e.g., HPLC, TLC, GC) fingerprint profiles, presence of a "marker" constituent, etc. In certain embodiments, the herbal composition is prepared by following the FDA's "Guidance for Industry Botanical Products", the entirety of which is incorporated herein by reference. The herbs may also be checked for the presence of pesticide residues, heavy metal content, etc. to ensure the safety of the final product.

As is appreciated by those skilled in this art, a variety of techniques are well known in the art for extracting, isolating, and/or purifying individual active components of the particular herbs. The present invention encompasses both the identification of such active components as described herein and the incorporation of such components into the formulas of the present invention as described herein.

Herbal Compositions

The three herbs of the herbal formula of the present invention, Ling-Zhi, Ku-Shen, and Gan-Cao, are known and have been characterized individually. Specifically, Ling-Zhi was identified as the fruiting body of *Ganoderma tsugae* (*Polyporaceae*), Ku-Shen as the root of *Sophora flavescent Ait* (*Leguminosae*), and Gan-Cao as the root and rhizome of *Glycyrrhiza uralensis* Fisch (*Leguminosae*). Their individual characteristics are summarized below in Table 1.

TABLE 1

Characteristics of Ling-Zhi, Ku-Shen, and Gan-Cao

| Information | Herbal medicine | | |
|---|---|---|---|
| Chinese name | Ling-Zhi | Ku-Shen | Gan-Cao |
| Synonyms | Reishi | Lightyellow *sophora* root | Licorice root |
| Pharmaceutical name | *Ganoderma* | Radix Sophorae Flavescentuis | Radix *Glycyrrhiza* |
| Plant Species Information | *Ganoderma Tsugae* Murr | *Sophora flavescent* Ait | *Glycyrrhiza uralensis* Fischer. |
| Part used | Fruiting body | Root | Root and rhizome |
| Family | Polyporaceae | Leguminosae | Leguminosae |
| Geographic location | Hubei | Shangxi | Inner Mongolia |
| Harvest season | Autumn | Autumn | Autumn |
| General Processing | Clean and dry in the shade or in oven at 40-50° C. | Remove the remains of rootstock and rootlet, wash clean, soak briefly cut into thick slices and dry | Eliminate foreign matter, wash clean, soften thoroughly, cut into thick slices and dry |
| Traditional Uses | General weakness, cough, asthma, insomnia, indigestion | dysentery, jaundice, pruritis edema, dysuria, eczema | sore throat, cough |
| Modern Uses | Nightmares, neurasthenia, coronary heart disease, arrhythmia, hyperlipidemia, hypertension, chronic hepatitis, chronic bronchitis, asthma, leukocytopenia | chronic hepatitis B, leukocytopenia | bronchitis, gastroduodenal ulcers |
| Daily Dose | 9-80 g | 3-27 g | 1.5-9 g |
| Caution & Contraindication | None | None | None |
| Toxicity-usual dose | None | None | None |
| Market | Yes | Yes | Yes |

Furthermore, certain chemical constituents of each of the three herbs that comprise the formulas of the present invention have been described. For example, it has been determined that the herb Ling-Zhi is made up of various polysaccharides, nucleotides, alkaloids, steroids, and triterpenoids. Such triterpenoids include Ganoderic acid A, Ganoderic acid B, Ganoderic acid C, and Ganoderic acid D, as shown below.

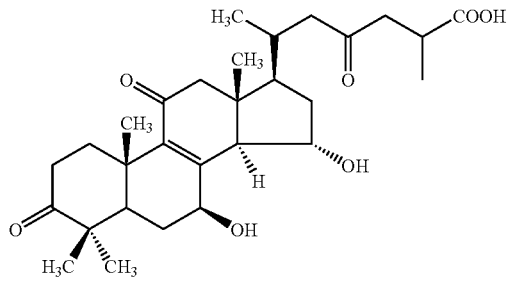

Ganoderic acid A

-continued

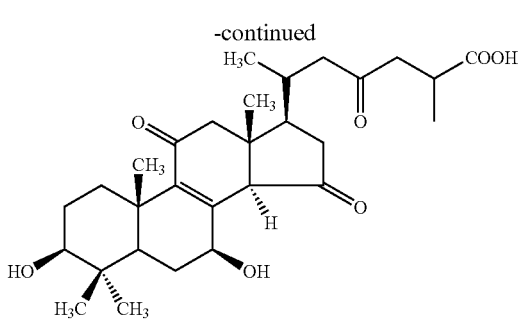

Ganoderic acid B

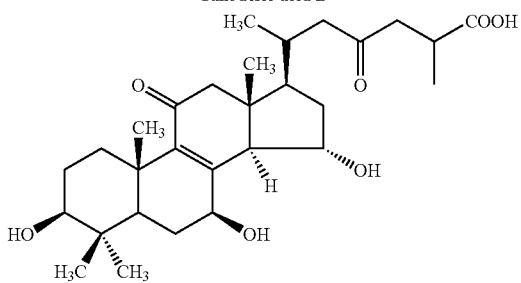

Ganoderic acid C

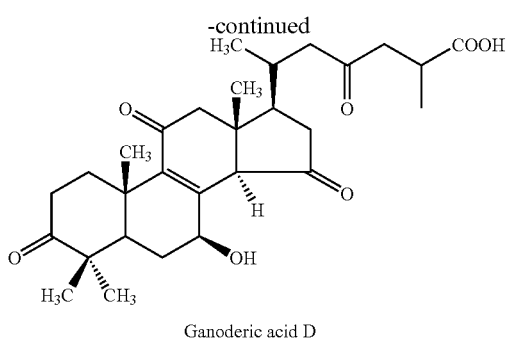

Ganoderic acid D

The herb Ku Shen has various alkaloid and flavanoid components. Such components include, but are not limited to, natrine, sophoridine, and kushenol A, as shown below.

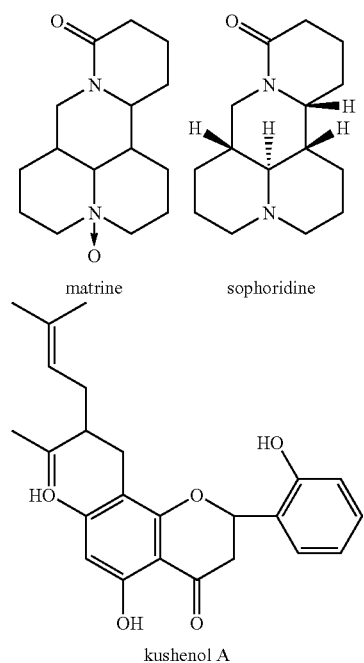

matrine   sophoridine kushenol A

It has been determined that the herb Gan-Cao contains various triterpene and flavenoid components. Such components include, but are not limited to, glycyrrhizic acid, glycyrrhetinic acid, deoxyglycyrrhetic acid I, deoxyglycyrrhetic acid II, liquiritic acid, glycyrrhetol, glabrolide, liquiritin, isoliquiritin, liquiritigenin, isoliquiritigenin, neo-liquiritin, and neoliquiritigenin.

In certain embodiments of the present invention, the herbal formula is prepared from about 9-80 grams of Ling-Zhi. Specifically, either about 9-80 grams of the herb Ling-Zhi itself is administered or an extract resulting from about 9-80 grams of Ling-Zhi is prepared and utilized as described hereinbelow.

In other embodiments of the present invention, the herbal formula is prepared from about 3-27 grams of Ku-Shen. Specifically, either about 3-27 grams of the herb Ku-Shen itself is administered or an extract resulting from about 3-27 grams of Ku-Shen is prepared and utilized as described hereinbelow.

In yet other embodiments of the present invention, the herbal formula is prepared from about 1.5-9 grams of Gan-Cao. Specifically, either about 1.5-9 grams of the herb Gan-Cao itself is administered or an extract resulting from about 1.5-9 grams of Gan-Cao is prepared and utilized as described hereinbelow.

In certain other embodiments, the herbal formula of the present invention consists of about 85% Ling-Zhi, about 8.5% Ku-Shen, and about 6.5% Gan-Cao.

The details of isolating and characterizing each of the herbs of the present invention are set forth below.

Isolation of Active Components

Individual active components of the herbs or herbal formulations may be identified as described herein and may be isolated and/or purified using any techniques known in the art. The active component may be purified from the herb itself in any form (e.g., fruit, seed, spore, flower, leaves, stalk, root, rhizomes, etc.), the culture media of the organism, the decoction of a mixture of the present herbal combination, etc. Various techniques that may be employed in the purification include filtration, selective precipitation, extraction with organic solvents, extraction with aqueous solvents, column chromatography, high performance liquid chromatography (HPLC), etc. (Zubrick, The Organic Chem Lab Survival Manual Third Edition New York: John Wiley & Sons, Inc., 1992; Scopes Protein Purification Principles and Practice (2nd ed.), New York: Springer-Verlag, 1987; each of which is incorporated herein by reference). As would be appreciated by one of skill in the art, the active components may be proteins, peptides, nucleic acids, natural products, terpenes, alkaloids, proteoglycans, polysaccharides, lipids, triglycerides, etc., and combinations thereof, and therefore, the purification procedure would depend on the nature of the component being purified.

According to certain embodiments, the herbal extracts are those using an isolated fraction from one or more herbs of the present invention. An isolated fraction means in this sense a subsidiary amount of herbal substances which has been removed, for example, by chromatographic means, distillation, precipitation, extraction, filtration or in other ways from the herb itself. In other embodiments, the herbal extracts and fractions are removed therefrom by chromatography, distillation, precipitation, or extraction. Such extraction and isolation techniques are well known to one of ordinary skill in the art. The details of some of these techniques are set forth in the Examples section below.

According to other embodiments of the present invention, the presence and purity of the active compound is assessed by chemical methods including nuclear magnetic spectroscopy (NMR), mass spectroscopy, infrared spectroscopy (IR), ultraviolet visible spectroscopy, elemental analysis, polarimetry, refractometry, etc. Such methods of analysis are known to one of ordinary skill in the art.

Although certain exemplary embodiments are described above and herein, it will be appreciated that the herbal formulas of the invention can be prepared according to the methods described generally above using appropriate starting materials by methods generally available to one of ordinary skill in the art.

Pharmaceutically Acceptable Compositions

1. Active Components

As discussed above, the present invention provides an herbal formula that is useful for the treatment of asthma. Accordingly, in another aspect of the present invention, pharmaceutically acceptable compositions are provided, wherein these compositions comprise the herbal formula as described herein, and further comprise a pharmaceutically acceptable carrier, adjuvant, or vehicle. In certain embodiments, these compositions optionally further comprise one or more additional therapeutic agents.

Other embodiments contemplated by the present invention include those where any active component, or combination thereof, is provided in said pharmaceutically acceptable composition. Such active components, and combinations thereof, may be provided by any methods known to one of ordinary skill in the art and by the methods described herein.

Further embodiments contemplated by the present invention include those where extracts, or lyophilates thereof, are provided in said pharmaceutically acceptable composition.

In certain embodiments, the present herbal formulas, extracts thereof, and pharmaceutically acceptable compositions thereof are administered orally. However, other routes of administration may also be utilized. For example, in some embodiments of the invention, pharmaceutical compositions may be delivered to mucous membranes, for example, by inhalation or injection. In general, the pharmaceutically acceptable compositions of the present invention can be administered to humans and/or to other animals, orally, rectally, parenterally, intracisternally, intravaginally, intraperitoneally, topically (as by powders, ointments, or drops), bucally, or as an oral or nasal spray.

2. Adjuvants

A variety of compounds are known in the art to have specific or general immunostimulatory effects. Such compositions are commonly referred to as "adjuvants". A large number of adjuvant compounds is known; a useful compendium of many such compounds is prepared by the National Institutes of Health and can be found on the world wide web (http:/www.niavd.nih.gov/daids/vaccine/pdt/compendium/pdf, incorporated herein by reference; see also Allison Dev. Biol. Stand. 92:3-11, 1998; Unkeless et al. Annu. Rev. Immunol. 6:251-281, 1998; Phillips et al. Vaccine 10:151-158, 1992; each of which is incorporated herein by reference). Adjuvants are characterized by an ability to stimulate Th1 responses preferentially over Th2 responses and/or to downregulate Th2 responses. In fact, in certain embodiments of the invention, adjuvants that are known to stimulate Th2 responses are avoided. Particularly adjuvants include, for example, preparations (including heat-killed samples, extracts, partially purified isolates, or any other preparation of a microorganism or microorganism component sufficient to display adjuvant activity) of microorganisms such as *Listeria monocytogenes* or others (e.g., Bacille Calmette-Guerin [BCG], *Corynebacterium* species, *Mycobacterium* species, *Rhodococcus* species, *Eubacteria* species, *Bortadella* species, and *Nocardia* species), and preparations of nucleic acids that include unmethylated CpG motifs (see, for example, U.S. Pat. No. 5,830,877; and published PCT applications WO 96/02555, WO 98/18810, WO 98/16247, and WO 98/40100, each of which is incorporated herein by reference). Other adjuvants reported to induce Th1-type responses and not Th2-type responses include, for example, Aviridine (N,N-dioctadecyl-N'N'-bis (2-hydroxyethyl)propanediamine) and CRL 1005.

In some embodiments of the invention, the adjuvant is associated (covalently or non-covalently, directly or indirectly) with the herbal formulation so that adjuvant and formulation can be delivered substantially simultaneously to an individual, optionally in the context of a single composition. In other embodiments, the adjuvant is provided separately. Separate adjuvant may be administered prior to, simultaneously with, or subsequent to herbal formulation administration. Where adjuvant and formulation are provided together, any association sufficient to achieve the desired immunomodulatory effects may be employed.

3. Carriers

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

4. Dosage Forms and Formulations

Liquid dosage formulations include, but are not limited to, pharmaceutically acceptable emulsions, microemulsions, solutions, suspensions, syrups and elixirs. In addition to the herbal formula, or active component(s) derived therefrom, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfaryl alcohol, polyethylene glycols and fatty acid esters of sorbitan, and mixtures thereof. Besides inert diluents, the liquid dosage forms can also include, for example, wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it may be desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms may be made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are include suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms (e.g. for oral administration) include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The herbal formula, or active components derived therefrom, of the present invention can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose, or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of the herbal formula, or active components derived therefrom, of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of the herbal formulation to the body. Such dosage forms can be made by dissolving or dispensing the compound in the proper medium. Absorption enhancers can also be used to increase the flux of the herbal formulation across the skin. The rate can be controlled by either providing a rate controlling membrane or by dispersing the compound in a polymer matrix or gel.

In certain embodiments, the herbal formula, or active components derived therefrom, of the present invention, or composition thereof, may be administered as a lyophilate, an aqueous solution, an alcoholic solution, or a syrup. One of ordinary skill in the art would recognize that the preparation of the present herbal formula as a lyophilate is accomplished directly by lyophilizing an aqueous extract of said herbal formula or, alternatively, a partially aqueous extract. By "partially aqueous" is meant that the herbal extract is obtained by a solution that contains water but is not entirely water. Such partially aqueous solutions that are amenable to lyophilization are known in the art. According to an alternate embodiment, the herbal extract is obtained in alcohol, such as ethanol, or other suitable solvent and that solvent is removed and replaced thereby with water. The resulting aqueous solution is then subjected to lyophilization to obtain the lyophilate of the herbal formula for administration.

In other embodiments, the herbal formula of the present invention is formulated into a syrup for pediatric use. Such syrups may include additional flavors and/or colorants to aid in the administration to children. Additionally, the present invention contemplates the preparation of an herbal tea. Such a tea can be prepared by dissolving or steeping the herbs of the present invention in the proper medium, such as hot water.

Uses of the Herbal Formulation and Pharmaceutically Acceptable Compositions Thereof In yet another aspect of the present invention, a method for treating or lessening the severity of asthma is provided, wherein said method comprises administering an effective amount of an herbal formula, or a pharmaceutically acceptable composition thereof, to a patient in need thereof. In certain embodiments of the present invention, an "effective amount" of the herbal formula or pharmaceutically acceptable composition thereof is that amount effective for alleviating or attenuating one or more symptoms associated with asthma.

The herbal formula and compositions thereof, according to the method of the present invention, may be administered using any amount and any route of administration effective for treating or lessening the severity of asthma. The exact amount required will vary from subject to subject, depending on the species, age, and general condition of the subject, the severity of the infection, the particular agent, its mode of administration, and the like. The herbal formula of the invention may be formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The pharmaceutically acceptable compositions of this invention can be administered to humans and animals orally, rectally, parenterally, intracisternally, intravaginally, intraperitoneally, topically (as by powders, ointments, or drops), bucally, as an oral or nasal spray, or inhaled. In certain embodiments, the herbal formula of the invention may be administered orally or parenterally at dosage levels of about 0.01 mg/kg to about 50 mg/kg and, alternatively, from about 1 mg/kg to about 25 mg/kg, of subject body weight per day, one or more times a day, to obtain the desired therapeutic effect.

The present invention relates to an herbal formula for the treatment of asthma, wherein said formula consists of three herbs selected from Ling-Zhi, Ku-Shen, and Gan-Cao. In particular, the present invention provides methods of treating or lessening the severity of asthma and/or asthma-related symptoms in a patient in need thereof comprising the step of administering to said patient an herbal formula of the present invention.

Another embodiment of the present invention relates to methods, as described herein, in which one or more chemical substances, in particular active substances, isolated from the herbs are used. By these are meant in particular also single substances isolated from one or more of Ling-Zhi, Ku-Shen, and/or Gan-Cao extracts, so-called natural substance isolates, as are also known, for example, to one or ordinary skill in the art. The use of these isolated active substances has the advantage that it is generally necessary to use considerably smaller amounts of substance and, moreover, more specific effects are often achieved than with whole extracts or tablets.

Without wishing to be bound by any particular theory, the herbal formulas and compositions thereof are particularly useful for treating or lessening the severity of a disease, condition, or disorder where one or more of suppressing GATA-3 and activation of memory Th2 cells is implicated in the disease, condition, or disorder. Accordingly, another embodiment of the present invention relates to a method of suppressing GATA-3 in a patient in need thereof, wherein said method comprises administering to said patient an herbal formula of the present invention or pharmaceutically acceptable composition thereof. Yet another embodiment relates to a method of suppressing the activation of memory Th2 cells in a patient in need thereof, wherein said method comprises administering to said patient an herbal formula of the present invention or pharmaceutically acceptable composition thereof.

The present herbal formulas and pharmaceutically acceptable compositions thereof may be employed to treat existing asthmatic symptoms (i.e., to reduce the severity, intensity, and/or duration of such symptoms). In such cases, the formulas or compositions thereof are administered to an individual after asthmatic symptoms have developed.

Alternatively or additionally, the composition may be used to prevent or delay the onset of symptoms in an individual who has previously suffered asthmatic attacks, or to reduce the severity, intensity, or duration of subsequently-developed symptoms. In certain embodiments, one or more antigens have been identified that is known to have induced, or at least to be correlated with, the onset of prior asthmatic attacks. In such cases, the present formulas and pharmaceutically acceptable compositions thereof are administered either prior to the onset of symptoms after a subsequent encounter with the antigen, or prior to the encounter.

The present formulas and compositions thereof may also be administered prior to the development of asthmatic sensitivity to a particular antigen. In certain embodiments, the compositions are administered substantially concurrently with exposure to an antigen that has not previously been associated with an asthmatic reaction in the individual. Without wishing to be bound by any particular theory, we propose that the present formulas and pharmaceutically acceptable compositions thereof may encourage the individual to adopt a Th1 response to the antigen. Given the mutually inhibitory aspects of Th1 and Th2 responses, the initial development of a Th1 response may inhibit, delay, or prevent subsequent Th1 reactions that could otherwise result in asthmatic and symptoms.

In other embodiments of the present invention, said formula is administered in combination with one or more additional therapeutic agents. For example, the herbal formulas of the present invention may be administered in combination with corticosteroids (e.g., inhaled, injected, or orally delivered corticosteroids), bronchodilators, etc. used to treat asthmatic symptoms.

In some cases, in will be desirable to provide the present herbal formulations in combination with one or more cytokines or inducing agents, to promote and/or reflect a reduction in Th2 responses and/or an increase in Th1 responses to the relevant antigen. In certain embodiments of the invention, herbal formulations are provided in combination with one or more Th1 stimulating cytokines (e.g., IL-12, IL-2, IL-18, IL-1$\beta$ or fragments thereof, IFN$\alpha$, and/or IFN$\gamma$, etc.) and/or one or more Th1 inducing agents (e.g., factors such as LPS, CD40, CD40 ligand, BCGs, oligonucleotides containing CpG motifs, TNF$\alpha$, and microbial extracts such as preparations of *Staphylococcus aureus*, heat killed *Listeria*, etc.). Alternatively or additionally, the herbal formulations may be provided in combination with one or more Th1 cytokines (e.g., IL-1$\beta$, IL-2, IL-12, IL-18, IFN$\alpha$, IFN$\gamma$, TNF$\beta$, etc.). In certain embodiments, said cytokines are administered within the pharmaceutically acceptable composition of the present invention, thus forming a single dosage form. In other embodiments, said cytokines are administered contemporaneously with the pharmaceutically acceptable composition of the present invention as a separate dosage form.

It will also be appreciated that the herbal formulas and pharmaceutically acceptable compositions of the present invention can be employed in combination therapies, that is, the herbal formulas of the present invention and pharmaceutically acceptable compositions thereof can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, the herbal formula of the present invention may be administered concurrently with another agent used to treat the same disorder), or they may achieve different effects (e.g., control of any adverse effects). As used herein, additional therapeutic agents that are normally administered to treat, lessen the severity of, or prevent a particular disease, or condition, are known as "appropriate for the disease, or condition, being treated."

The herbal formulas of the present invention may be administered to a subject in combination with one or more other therapeutic treatments. For example, corticosteroid administration is an established and accepted treatment for asthma. Thus, the herbal formulations of the present invention may desirably be administered in combination with standard or reduced corticosteroid treatments, whether inhaled or systemic. The herbal formulations of the present invention may also be administered in combination with additional therapeutic immunotherapy or rush immunotherapy. Immunotherapies are typically administered in order to induce tolerance in a sensitized individual (for a more detailed description of immuotherapy, please see U.S. Provisional Patent Application, U.S. Ser. No. 60/213,765, filed Jun. 23, 2000; incorporated herein by reference).

Other therapeutic agents, known for the treatment of asthma, may be administered with the herbal formulas, or pharmaceutically acceptable compositions thereof, of the present invention. Such agents also include, but are not limited to, bronchodilators, either inhaled or systemic including albuterol and Ventolin®, leukotriene inhibitors, including Singulair®, and combination therapy such as Advair®, to name a few. It will be appreciated that these therapeutic agents may be administered with the present herbal formulas, and pharmaceutically acceptable compositions thereof, in a single dosage form or separately.

The present herbal formulas may be administered, whether alone or in combination with one or more other agents or compounds, in the context of an encapsulated system. A variety of encapsulation systems are known in the art (see, for example, discussions in U.S. Ser. No. 60/169,330, filed Dec. 6, 1999, and incorporated herein by reference); any such system may be employed in accordance with the present invention. In certain embodiments of the invention, the encapsulation material itself may offer adjuvant activity. Also, encapsulation systems may desirably be associated with one or more targeting agents that facilitate delivery of the present compositions to relevant sites (e.g., mucosal membranes).

The amount of additional therapeutic agent present in the compositions of this invention will typically be no more than the amount that would normally be administered in a composition comprising that therapeutic agent as the only active agent. In certain embodiments, the amount of additional therapeutic agent in the presently disclosed compositions will range from about 50% to 100% of the amount normally present in a composition comprising that agent as the only therapeutically active agent.

These and other aspects of the present invention will be further appreciated upon consideration of the following Examples, which are intended to illustrate certain particular embodiments of the invention but are not intended to limit its scope, as defined by the claims.

EXAMPLES

The effects of herbal formulas of the present invention and pharmaceutically acceptable compositions thereof may be assessed in humans or in any available in vivo or in vitro model system. Animal models are particularly useful for the identification, characterization, and analysis of a particular composition's effects. Ideally, a model system should reflect closely at least some aspect of the disease pathology in man (or in another organism to which composition of the present invention is to be administered for the treatment of asthma or allergy), should be reliable and reproducible, should allow objective measurements of one or more physiologically-relevant parameters, should respond to one or more known therapeutic agents in a manner similar to that observed in man (or the suffering organism), and/or should offer a large number of reagents with which the immune system can be analyzed.

A variety of animal models, including those in guinea pigs, rabbits, sheep, dogs, monkeys, and mice have been developed that can usefully be employed to characterize the herbal formulas of the present invention and pharmaceutically acceptable compositions thereof (see, for example, Kay (ed.) Allergy and Allergic Diseases Blackwell Science, Ltd., Oxford. pp. 1037-1110, 1997; McCaskill et al. "Anaphylaxis Following Intranasal Challenge of Mice Sensitized with Ovalbumin" Immunology 51:669-677, 1984; U.S. patent application Ser. No. 09/518,246, filed Mar. 3, 2000; each of which is incorporated herein by reference).

Where a mouse model is employed, those of ordinary skill in the art will recognize that the particular mouse strain or route of administration of sensitizing antigen may not be critical in developing a mouse model system for use in characterizing the herbal formulas of the present invention. For example, Renz et al. have described a BALB/c mouse sensitized with aerosolized ovalbumin over a 10-day period (Renz et al., J. Exp. Med. 177:1175, 1993; incorporated herein by reference). These mice show elevated levels of ovalbumin-specific IgE and infiltration of eosinophils into the airway following bronchial challenge. Wills-Karp et al. have described an asthmatic A/J mouse model sensitized by intraperitoneal administration of antigen, followed by intratracheal challenge (Gavett et al., Am. J. Respir. Cell Mol. Biol. 10:587, 1994; Keane-Myers et al., J. Immunol. 161:919, 1998; Wills-Karp et al., Science 282:2258, 1998; Grunig et al., Science 282:2261, 1998; each of which is incorporated herein by reference). In certain embodiments, the sensitizing antigen is administered to the animal via the same route the animal would encounter the allergen in nature (e.g., oral for food allergens, IV or parenteral for venoms, inhaled for pollens or dust allergens, intradermal for latex). In another embodiment, the mouse is sensitized to the allergen using alum as an adjuvant.

We herein describe a conalbumin-allergic AKR/J mouse in which IgE significantly increased following intraperitoneal sensitization, and BALF eosinophils were increased at 12 hour and peaked at 72 hours following i.t. challenge. This model closely mimics the late phase response of human asthma and is particularly useful in the characterization of the herbal formulas of the present invention (Li et al., J. Immunol. 160:1378, 1998; incorporated herein by reference). Those of ordinary skill in the art will appreciate that any of a variety of mouse or other animal model systems can be developed and/or utilized in accordance with the present invention.

Example 1

Preparation of Extracts of Ling-Zhi, Ku-Shen, and Gan-Cao: All raw herbal materials used in our preliminary study were provided by Institute of Medicinal Plant Development, Chinese Academy of Medical Sciences, Beijing, China. Based on the morphological characteristics of the plants, Ling-Zhi was identified as the fruiting body of *Ganoderma tsugae* (Polyporaceae), Ku-Shen as the root of *Sophora flavescent* Ait (Leguminosae), and Gan-Cao as the root and rhizome of *Glycyrrhiza uralensis* Fisch (Leguminosae). The herbs were soaked together in water (w/v: 1 g:10 ml) for 40 minutes at room temperature and then boiled for 45 minutes over medium heat. After collecting the decoction, the herbs were then boiled in the same volume of water for an additional 45 minutes. The two decoctions were combined, filtered, and lyophilized. The results of the above-described extraction are summarized below in Table 2.

TABLE 2

Results of Preparation of Herbal Extracts

| Name | Quantity of raw herbal materials (g) | Volume of water added (ml) | Extracts (g) | Extracts (g) obtained from 100 g of herbs |
|---|---|---|---|---|
| ASHMI | 94 | 940 | 8.31 | 8.84 |
| Ling-Zhi | 80 | 800 | 4.36 | 5.45 |
| Ku-Shen | 80 | 800 | 18.58 | 23.23 |
| Gan-Cao | 60 | 600 | 21.54 | 35.90 |

Example 2

HPLC Fingerprint of ASHMI: The formula containing Ling-Zhi extract, Ku-Shen extract and Gan-Cao extract ("ASHMI") was subject to HPLC analysis and a three-dimensional HPLC pattern of the formula was obtained using the following methods.

Materials and reagents: A sample of ASHMI extract containing Ling-Zhi extract, Ku-Shen extract and Gan-Cao was prepared as described above at Example 1. Purified glycyrrhizic acid and liquiritin were provided by Institute of Medicinal Plant Development, Chinese Academy of Medical Sciences, China. HPLC grade acetonitrile and methanol were purchased from Acros organics and Fisher Scientific.

Chromatographic conditions: The HPLC system consisted of a Waters® alliance system with a 996 photodiode-array detector (scan from 200400 nm). Data were acquired and processed with the Empower® software system. HPLC analysis was performed on a Zorbax SB-$C_{18}$ column (5 μm, 4.6 mm×150 mm i.d.) with a Zorbax ODS guard column from Agilent Technologies. The column temperature was set to 30° C. and a mixture of acetonitrile ("solvent A") and 0.01M solution of phosphoric acid ("solvent B") were used as the mobile phase. Gradient chromatography was carried out in linear gradient mode (2%-48% of A for 0~75 min, 48%~70% of A for 75~79 min) with a flow-rate of 1 ml/min.

Preparation of reference solution: 1.0 mg of glycyrrhizic acid and liquiritin were added into 5 ml volumetric flasks and methanol added to volume. 10 μl of each solution was injected into the HPLC system.

Preparation of samples for analysis: 100 mg of ASHMI extract was dissolved in 10 ml of $H_2O$, and then extracted with 5 ml of n-butanol five times. The combined extracts were evaporated in a water bath. The residue was dissolved in 50% methanol and the solution transferred to a 2 ml volumetric flask and diluted to volume. 10 μl of the resulting solution was injected into the HPLC system. 52.5 mg, 22.4 mg and 26.0 mg of Ling-Zhi, Ku-Shen and Gan-Cao extracts, respectively, were weighed (calculated on ratio of individuals in ASHMI and the yield of extracts) and each sample was prepared as above. 10 μl of the resulting solution was injected into HPLC system.

Figure 2:
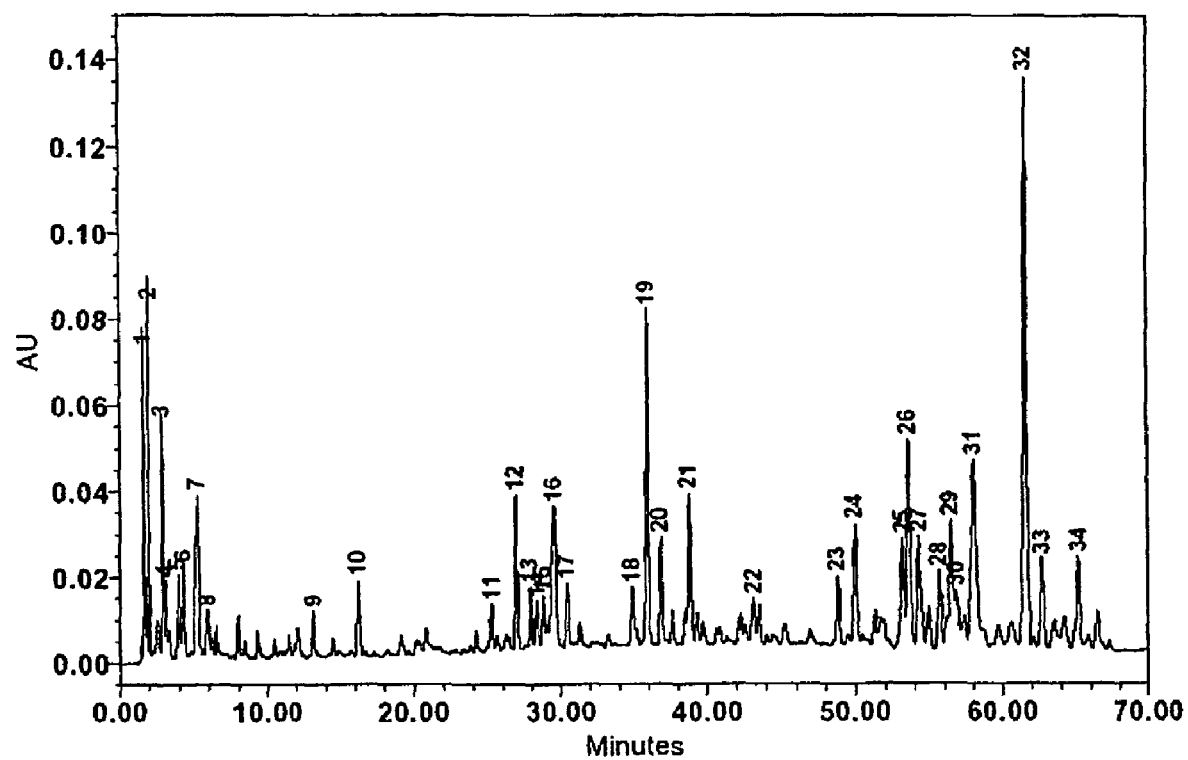
FIG. 2 depicts the two-dimensional HPLC fingerprint of ASHMI as detected at 254 nm.

HPLC fingerprint of ASHMI: The ASHMI extract was subjected to HPLC analysis and a three-dimensional HPLC pattern of said extract was obtained. See FIG. 1. Results show chemical patterns obtained by Reverse-phase HPLC with diode array detectors (DAD) detection (scan from 200 to 400 nm). According to the on-line UV spectra, it was divided into three groups by retention time ($t_R$), ASH-a in 0-5 minutes; ASH-b in 5-45 minutes; ASH-c in 45~70 minutes. When absorbance was set to 254 nm, additional peaks, and better separation could be obtained. From the 2D-chromatographic fingerprint of ASHMI, 31 diagnostic peaks were observed. See FIG. 2. There are 5 diagnostic peaks (1-5) in Group ASH-a, 2 in Group ASH-b (6 and 7), and 24 in Group ASH-c (8-31). The ratio of the main peak areas is 6: 9:10:14:15:16: 19:21:26:27≈1.0:0.8:1.3:0.9:1.0:1.1:1.4:3.1:1.0:1.0. Except for peak 21, other major peaks share almost the same peak area. The related parameters including retention time ($t_R$), relative retention time, and percentage of area are listed in Table 3, below. Peak 2 in Table 3 is considered as a main peak because this peak appears at very early (2.45 min), where the peak area was often unstable in gradient elute.

TABLE 3

The HPLC Fingerprint Parameters of ASHMI

| Peak No. | $t_R$ (min) | Relative $t_R{}^a$ | Area % |
|---|---|---|---|
| 1 | 2.24 | 0.08 | 0.96 |
| 2 | 2.45 | 0.09 | 4.38 |
| 3 | 3.26 | 0.12 | 2.12 |
| 4 | 3.70 | 0.14 | 2.33 |

TABLE 3-continued

The HPLC Fingerprint Parameters of ASHMI

| Peak No. | $t_R$ (min) | Relative $t_R^a$ | Area % |
|---|---|---|---|
| 5 | 4.73 | 0.17 | 1.05 |
| 6 | 27.25 | 1 | 4.95 |
| 7 | 33.83 | 1.24 | 1.81 |
| 8 | 44.75 | 1.64 | 1.33 |
| 9 | 46.92 | 1.72 | 3.71 |
| 10 | 48.14 | 1.77 | 6.51 |
| 11 | 49.36 | 1.81 | 1.62 |
| 12 | 49.65 | 1.82 | 1.06 |
| 13 | 50.06 | 1.84 | 1.86 |
| 14 | 51.28 | 1.88 | 4.29 |
| 15 | 51.62 | 1.89 | 5.29 |
| 16 | 52.41 | 1.92 | 5.59 |
| 17 | 53.15 | 1.95 | 1.45 |
| 18 | 53.71 | 1.97 | 1.98 |
| 19 | 54.27 | 1.99 | 6.95 |
| 20 | 55.30 | 2.03 | 1.43 |
| 21 | 55.83 | 2.05 | 15.17 |
| 22 | 56.30 | 2.07 | 1.11 |
| 23 | 57.76 | 2.12 | 0.97 |
| 24 | 58.02 | 2.13 | 1.66 |
| 25 | 58.33 | 2.14 | 2.42 |
| 26 | 59.28 | 2.18 | 4.93 |
| 27 | 60.45 | 2.22 | 5.28 |
| 28 | 61.19 | 2.25 | 1.36 |
| 29 | 62.03 | 2.28 | 1.57 |
| 30 | 62.61 | 2.30 | 1.69 |
| 31 | 64.25 | 2.36 | 3.16 |

Example 3

Figure 3:
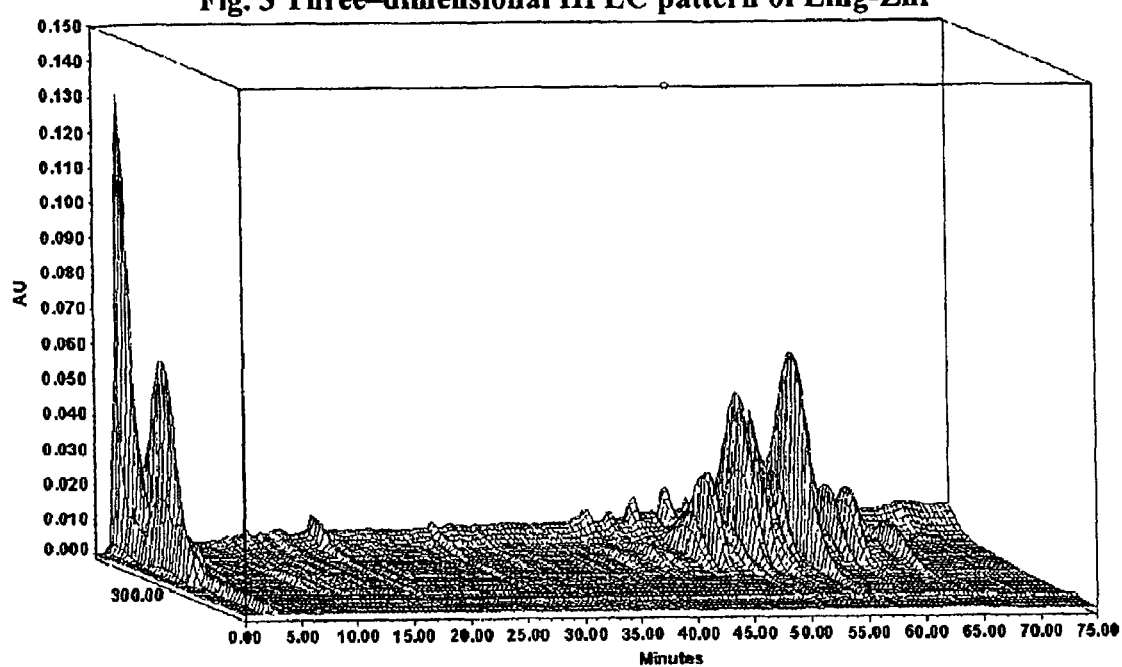
FIG. 3 depicts the three-dimensional LIPLC pattern of Ling-Zhi as obtained by Reverse-Phase HPLC using diode array detection.
Figure 4:
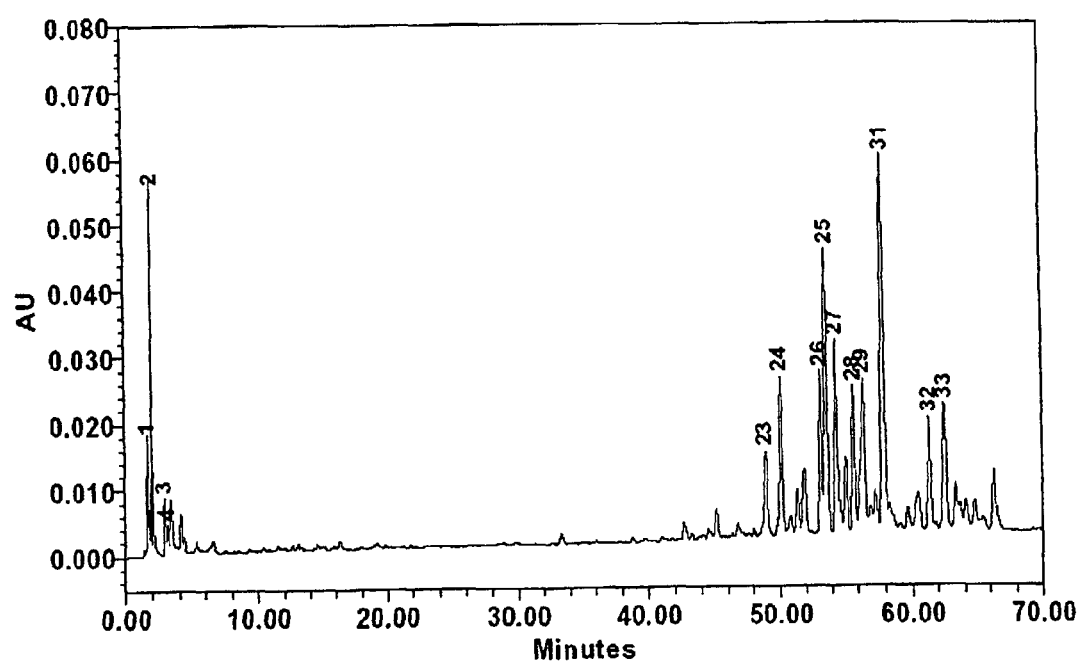
FIG. 4 depicts the two-dimensional HPLC fingerprint of Ling-Zhi as detected at 254 nm.

HPLC Fingerprint of Ling-Zhi: HPLC analysis of Ling-Zhi extract was carried out under the same condition as for ASHMI extract. The three-dimensional HPLC pattern of Ling-Zhi obtained was found to be characteristic for chemical constituents in Ling-Zhi extract. See FIG. 3. It displayed two well-separated groups of peaks. We labeled peaks in 0-5 min as Group L-a, and peaks in 40-70 min as Group L-b. The peaks in Group L-b gave similar UV spectra, suggesting that they have similar chemical structures. More peaks and better separation could be obtained by detecting at 254 nm. From the 2D-chromatographic fingerprint of Ling-Zhi, 19 diagnostic peaks were observed, 3 of them (1-3) appeared in Group L-a, and the others in Group L-b. See FIG. 4. The major diagnostic peaks, 6, 9, 10, 11, 14, 15, 17 and 18, all were located at Group L-b. Peak 15, the strongest one with 17% of peak area in whole profiles, was selected as a marker to locate and quantity other peaks. The ratio of peak area between these major peaks is: 6:9:10:11:14:15:17:18≈0.6:0.3: 0.4:0.5:0.5: 1.0:0.4:0.4. The fingerprint parameters including retention time ($t_R$), relative retention time, percentage of area are listed in Table 4, below.

TABLE 4

The HPLC Fingerprint Parameters of Ling-Zhi

| Peak No. | $t_R$ (min) | Relative $t_R^a$ | Area % |
|---|---|---|---|
| 1 | 1.81 | 0.03 | 2.44 |
| 2 | 2.60 | 0.05 | 2.38 |
| 3 | 3.82 | 0.07 | 1.99 |
| 4 | 44.76 | 0.80 | 2.00 |
| 5 | 46.93 | 0.84 | 4.34 |
| 6 | 48.15 | 0.86 | 9.35 |

TABLE 4-continued

The HPLC Fingerprint Parameters of Ling-Zhi

| Peak No. | $t_R$ (min) | Relative $t_R^a$ | Area % |
|---|---|---|---|
| 7 | 19.38 | 0.88 | 2.66 |
| 8 | 50.10 | 0.90 | 3.71 |
| 9 | 51.31 | 0.91 | 5.95 |
| 10 | 51.66 | 0.92 | 7.11 |
| 11 | 52.44 | 0.94 | 7.88 |
| 12 | 53.21 | 0.95 | 2.08 |
| 13 | 53.75 | 0.96 | 2.59 |
| 14 | 54.32 | 0.97 | 8.99 |
| 15 | 55.88 | 1 | 17.03 |
| 16 | 58.41 | 1.05 | 3.17 |
| 17 | 59.35 | 1.06 | 5.92 |
| 18 | 60.52 | 1.08 | 6.29 |
| 19 | 64.35 | 1.15 | 4.08 |

Note
$^a t_R$ of peaks/$t_R$ of Chemical Marker(peak 15);

Example 4

Figure 5:
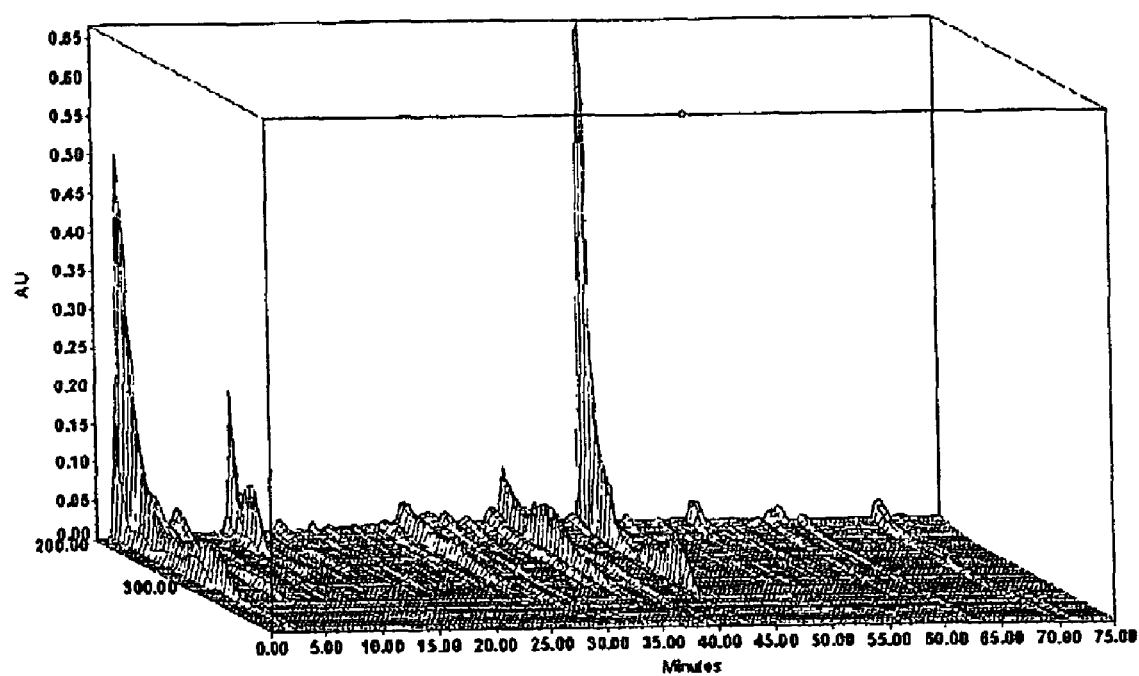
FIG. 5 depicts the three-dimensional MPLC pattern of Ku-Shen as obtained by Reverse-Phase HPLC using diode array detection.
Figure 6:
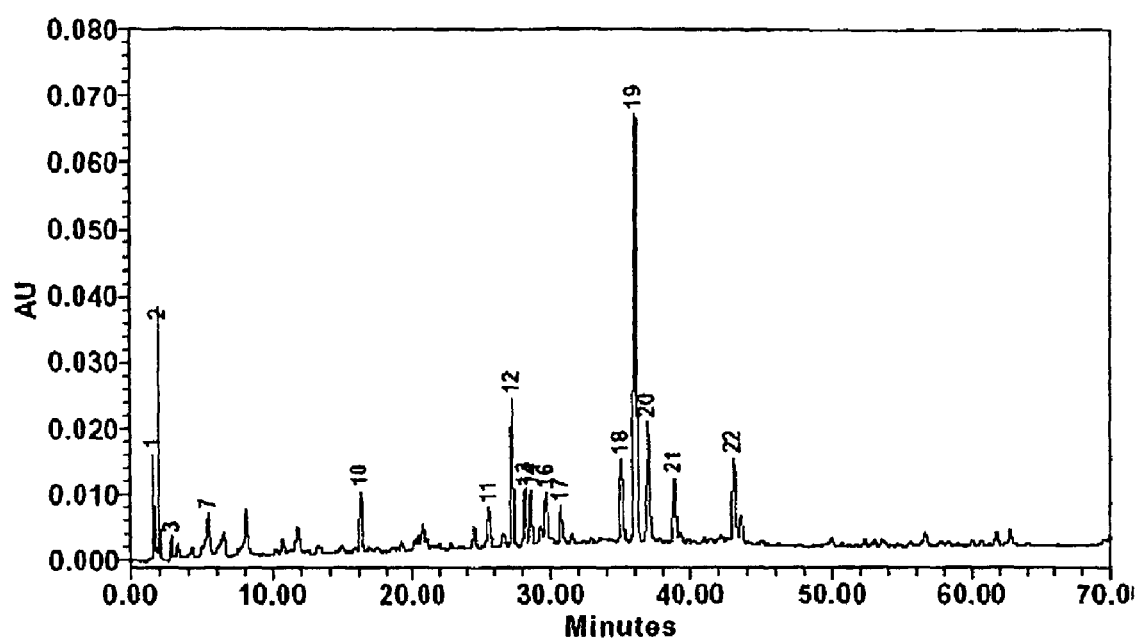
FIG. 6 depicts the two-dimensional HPLC fingerprint of Ku-Shen as detected at 254 nm.

HPLC Fingerprint of Ku-Shen: The same analysis program as described above at Example 3 was applied to investigate Ku-Shen extract. The three-dimensional HPLC pattern of Ku-Shen from 200 to 400 nm was obtained. See FIG. 5. Most constituents in Ku-Shen had the strongest absorbance at lower wavelengths such as 205 nm. However, many impurities, even solvents have strong absorbance at this wavelength. To obtain a unique profile related to Ku-Shen, we also used 254 nm as the detection wavelength which revealed 10 diagnostic peaks. See FIG. 6. The major peaks, 6 and 7, together possess 50% of the total peak area. The fingerprint parameters including retention time ($t_R$), relative retention time, and percentage of area are listed in Table 5, below.

TABLE 5

The HPLC Fingerprint Parameters of Ku-Shen

| Peak No. | $t_R$ (min) | Relative $t_R^a$ | Area % |
|---|---|---|---|
| 1 | 25.47 | 0.75 | 8.21 |
| 2 | 26.38 | 0.78 | 4.52 |
| 3 | 27.34 | 0.81 | 7.89 |
| 4 | 28.41 | 0.84 | 7.72 |
| 5 | 32.82 | 0.97 | 5.19 |
| 6 | 33.78 | 1 | 34.89 |
| 7 | 34.69 | 1.03 | 14.26 |
| 8 | 40.74 | 1.21 | 5.58 |
| 9 | 41.31 | 1.22 | 7.52 |
| 10 | 54.00 | 1.60 | 4.21 |

Example 5

Figure 7:
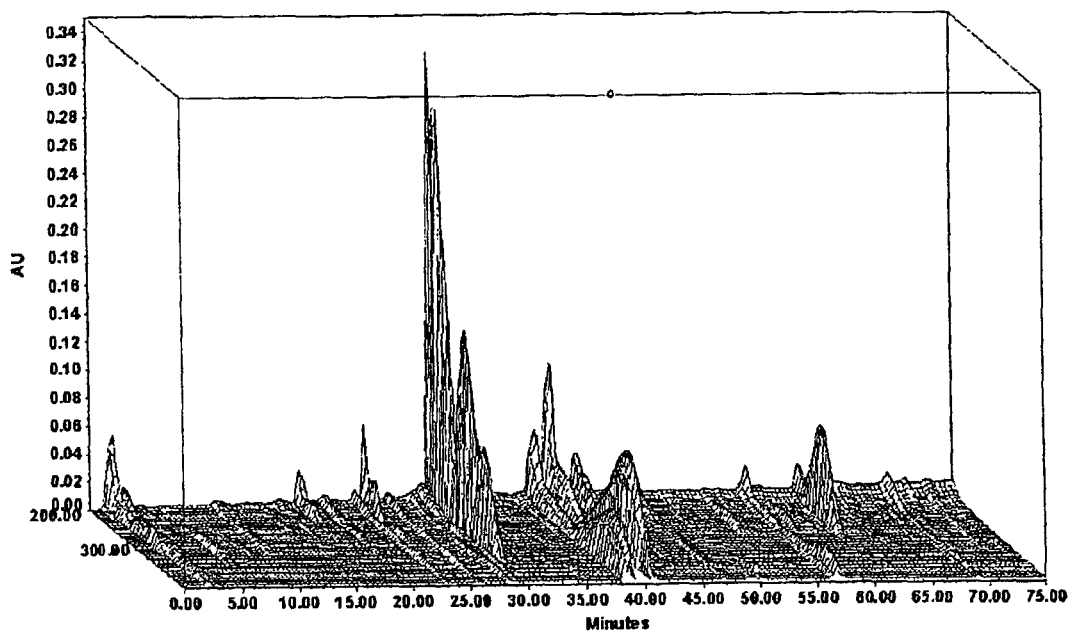
FIG. 7 depicts the three-dimensional HPLC pattern of Gan-Cao.
Figure 8:
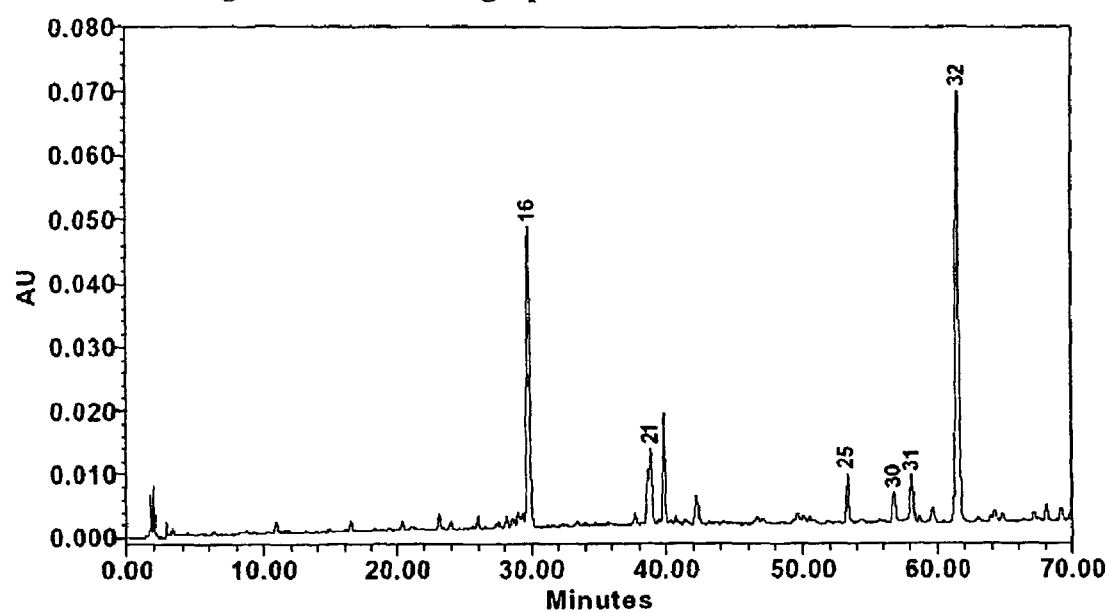
FIG. 8 depicts the two-dimensional HPLC fingerprint of Ku-Shen as detected at 254 nm.

Fingerprint of Gan-Cao: Gan-Cao extract was also subjected to the HPLC analysis as described for Example 3, above. We obtained a simple three-dimensional HPLC pattern for Gan-Cao which reveals only a single clear peak. See FIG. 7. To get more information on the chemical pattern, we generated 2D-HPLC fingerprint of Gan-Cao at 254 μm, and 6 diagnostic peaks were observed. See FIG. 8. Peak 3 is the strongest peak with 61.40% peak area in all 6 peaks. The ratio of peak 3 and 6 is approximately 4.4:1. The detailed fingerprint parameters are listed in Table 6, below.

TABLE 6

The HPLC Fingerprint Parameters of Gan-Cao

| Peak No. | $t_R$ (min) | Relative $t_R{}^a$ | Area % |
|---|---|---|---|
| 1 | 2.38 | 0.09 | 3.93 |
| 2 | 18.2 | 0.68 | 2.87 |
| 3 | 26.67 | 1 | 61.40 |
| 4 | 36.11 | 1.35 | 8.68 |
| 5 | 36.44 | 1.37 | 9.18 |
| 6 | 58.20 | 2.18 | 13.94 |

Example 6

Figure 9:
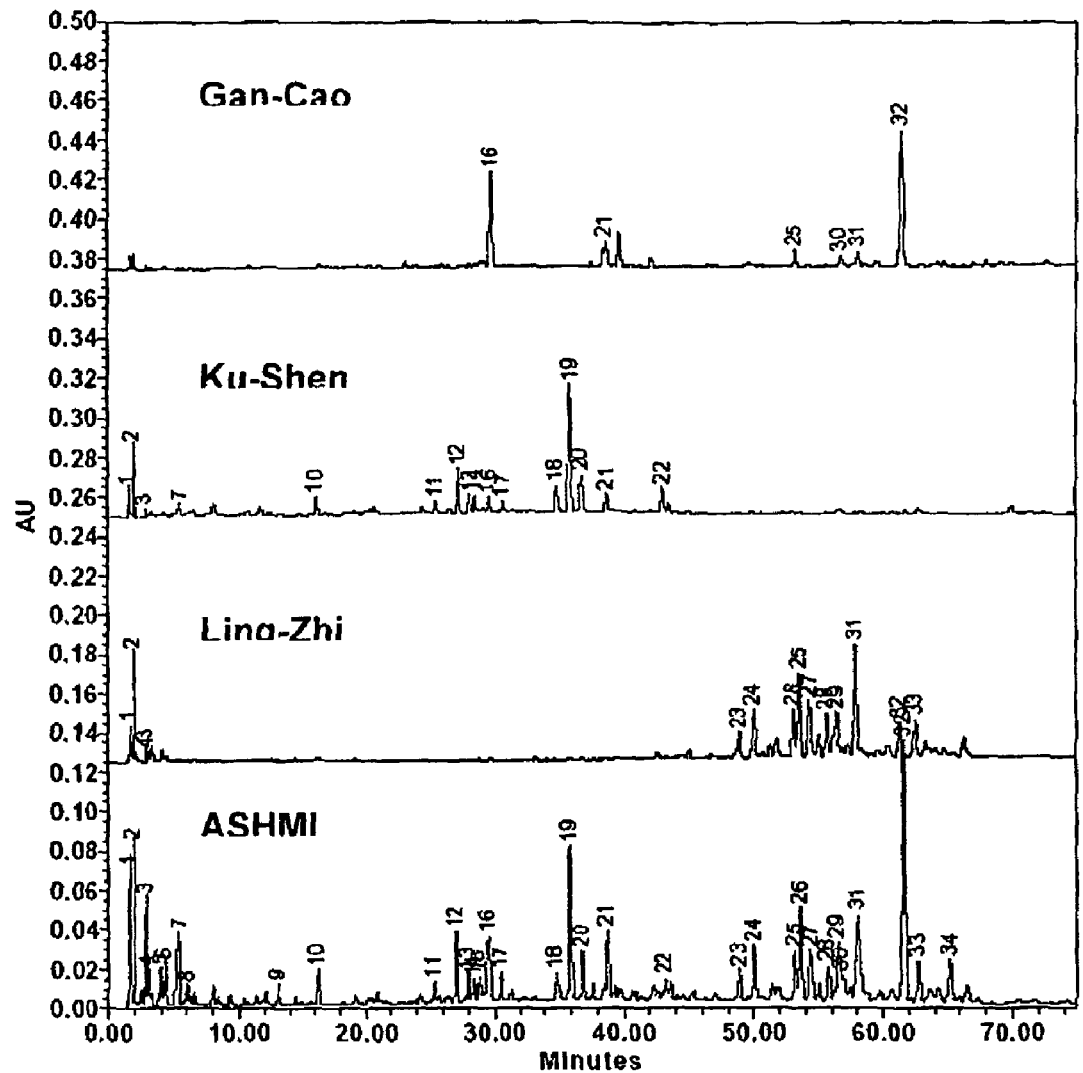
FIG. 9 depicts the two-dimensional HPLC profiles of ASHMI and its individual components.

Correlation of the ASHMI Fingerprint With Individual Herbs: The 2D-HPLC profiles (at 254 nm) of each of the individual herbs in parallel with that for the ASHMI were compared. See FIG. 9. By comparison of the on-line UV spectra and retention time ($t_R$), the diagnostic peaks 6-31 in the ASHMI fingerprint were correlated with its individual herbal medicines. The formula peaks 6 and 25 originated from Gan-Cao, whereas the peak 7 corresponds to Ku-Shen, and the other peaks from Ling-Zhi. In addition to the labeled peaks, some minor peaks may be of value for quality control. For example, the diagnostic peaks of Ku-Shen such as peak 1, 2, 3, 4, 7 are not labeled in the ASHMI fingerprint due to the low absorbance at 254 nm and the lower relative content in formula. However, we can still find these peaks in the ASH-b group fingerprint of the ASHMI fingerprint. The reference solutions of each chemical standard were injected into the HPLC system under the same HPLC conditions as samples. Based on the retention time and the on-line UV spectra of chemical markers, peaks 6 and 25 in the ASHMI sample were identified as liquiritin and glycyrrhetic acid.

Example 7

ASHMI Formula Preparation: For the following assays, the ASHMI extract utilized consists of the 3 herbal medicines, Ling-Zhi (Ganoderma) 40 grams, Ku-Sheer (Radix Sophorae Flavescentuis) 4 grams, and Gan-Cao (Radix Glycyrrhiza) 3 grams, for a total 47 g of raw herbs. This dose is equivalent to adult daily dose. All herbs are of Chinese origin as described. This ASHMI extract was prepared in our laboratory as follows. The herbs were soaked together in water (w/v: 1 g: 10 ml) for 60 minutes at room temperature and then boiled for 45 minutes over medium heat. After collecting the decoction, the herbs were again boiled in the same volume of water for an additional 45 minutes and combined with the first decoction, filtered and then lyophilized. The dried extract powders were stored in 50 ml plastic tubes at room temperature. The mouse daily dose was determined by a conversion table of equivalent dose ratios from humans to animals based on body surface area. Nine mg of a lyophilized decoction of the herbal formula is equivalent to the human adult daily dose.

Example 8

Figure 10:
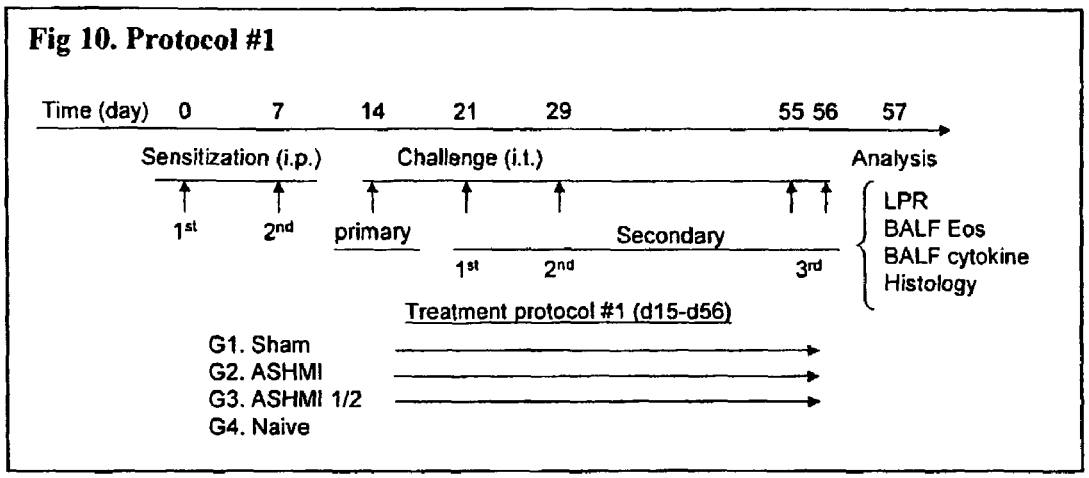
FIG. 10 depicts the details of dosing Protocol #1.

Antigen Sensitization/Challenge and Treatment with ASHMI: BALB/c mice (6 wk old, n=5-6/group) were sensitized twice (on days 0 and 7) i.p. with OVA (100 µg) in alum in 0.4 ml. One week following the last sensitization, mice received a primary i.t. challenge with OVA 50 µg in 50 µl PBS, and then received 2 secondary challenges (re challenge) at days 21 and 29, and a third secondary challenge 4 weeks later. Treatment began 1 day after the first i.t. challenge and continued for 6 weeks. Four groups (G) of mice were used in this experiment, and treated with either 0.5 ml of water as placebo (G1, placebo), or equivalent daily dose ASHMI at 4.5 mg in 0.5 ml of water, twice daily (9 AM and 3 PM) for consecutive 6 weeks (G2). An additional group of mice received a half daily dose (½) ASHMI at 2.25 mg, twice daily (G3). Naïve mice (G4, naïve) served as normal controls. See FIG. 10.

Example 9

Figure 11:
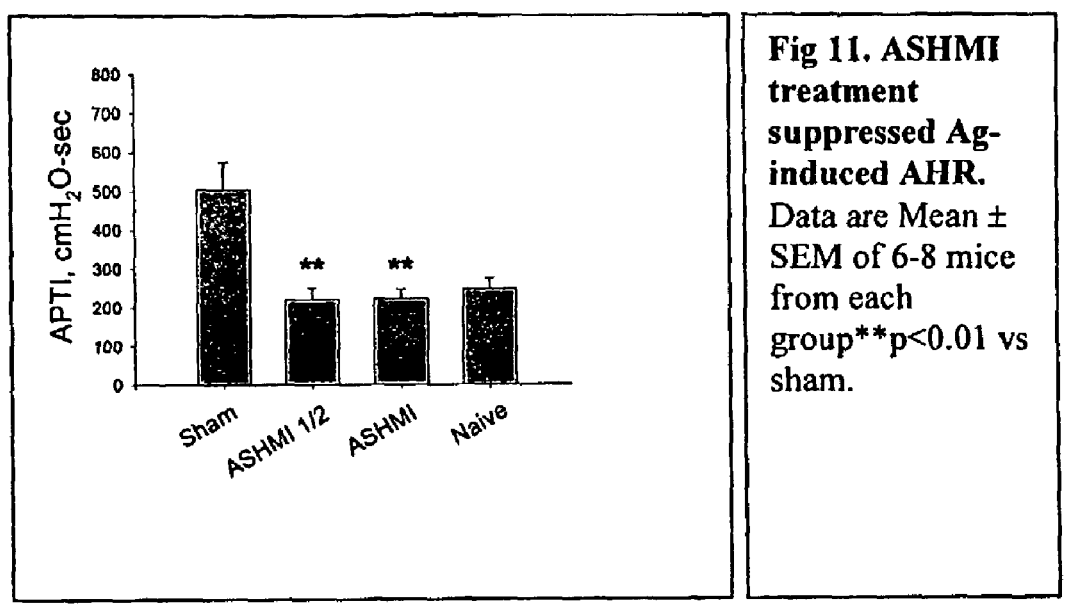
FIG. 11 shows the results of the suppression of Ag-induced AHR due to ASHMI treatment.

Suppression of Ag-Induced AHR: Two days following the last Ag-challenge, AHR was determined by measuring airway pressure changes over time following acetylcholine (Ach) challenge, and the results expressed as airway pressure time index APTI, $cmH_2O$-sec as previously described. APTI levels of placebo treated, Ag-sensitized/challenged mice were markedly higher than naive mice, indicating the induction of AHR. See FIG. 11. APTI levels in the daily dose and the half daily does ASHMI-treated groups were significantly lower compared to placebo-treated group ($p<0.05$ vs placebo respectively), and were essentially the same as naïve mice. These results demonstrated that, as compared to placebo treatment, the ASHMI virtually eliminated AHR in this model.

Example 10

Reduction of Ag-Induced Pulmonary Inflammation: To determine whether suppression of AHR was associated with reduced inflammation, we measured the total number of BALF leukocytes, and percent eosinophils in BALF as previously described. The total number of leukocytes in ASHMI normal daily dose and half daily dose treated groups were significantly lower compared to the placebo-treated group. While BALF from naïve mice contained virtually no eosinophils, BALF from the placebo-treated, Ag-sensitized, and challenged group contained 59% eosinophils. See FIG. 12. Both normal and half daily doses significantly reduced the number of eosinophils in BALF and the normal dose appeared to be more pronounced ($p<0.001$ and 0.01 vs placebo). These results suggest that ASHMI has anti-inflammatory properties.

Example 11

Lung Histology: As previously described, lungs from placebo-treated, Ag-sensitized/challenged mice contained large numbers of peribronchial and perivascular lymphocytes and eosinophils. In accord with BAL data, lungs from formula treated mice contained markedly fewer inflammatory cells. While numerous goblet cells were present in airways of placebo-treated group, few goblet cells, if any, were present in airways of the ASHMI treated group. See FIG. 13. These results demonstrate the remarkable suppressive effect of ASHMI on goblet cell hyperplasia.

Example 12

Figure 14:
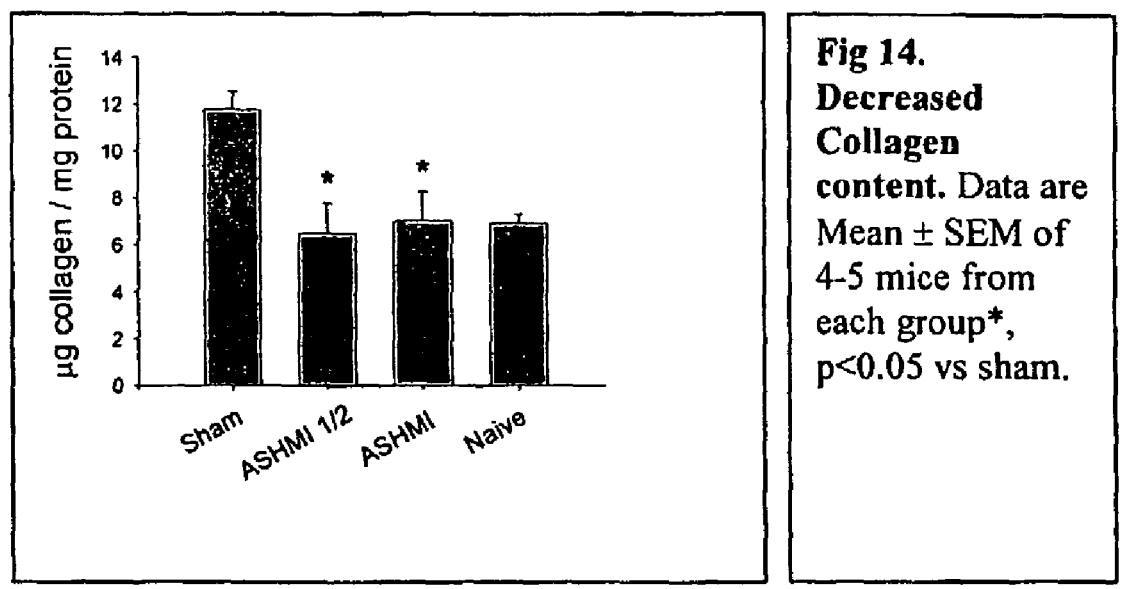
FIG. 14 shows the reduction of collagen content in ASHMI treated mice as compared to placebo-treated mice and naïve mice.

Lung Collagen Content: *Subepithlial fibrosis* is one of the major features of airway remodeling in chronic asthma. To determine whether ASHMI can improve some features of airway remodeling, we measured the collagen content of homogenized lung samples using the Sircol Collagen Assay (Biocolor, Ltd), a quantitative colorometric method employing a dye, which specifically binds to the (Gly-X-Y) triple-helical sequences of collagen. Collagen content of the placebo-treated group was significantly higher than that of naïve mice. See FIG. 14. In contrast, the collagen contents of the ASHMI treated groups, even in the half normal daily dose-treated group were significantly lower than in the placebo-treated group and were not different from the naïve control, indicating ASHMI completely inhibited collagen over production in this model of chronic asthma.

Example 13

Antigen Specific Serum IgE: Sera from each group of mice were obtained immediately after the APTI measurement. Serum antigen specific IgE levels measured as previously described were significantly, although not dramatically reduced in the normal daily dose ASHMI treated-group as compared with the placebo treated group ($p<0.05$ vs placebo). IgE levels in the half daily dose ASHMI treated group were also lower than the placebo-treated group, but did not reach statistical significance (data not shown). These results suggest that although the ASHMI suppression of IgE may be beneficial, this effect is not essential for the abrogation of late phase AHR. These results suggest that ASHMI might be useful for both IgE mediated and non-IgE mediated asthma.

Example 14

Contractile Responses of Tracheal Rings to Acetylcholine: Increased airway smooth muscle (ASM) contraction or reduced smooth muscle relaxation contribute to excessive airway narrowing and airway hyperresponsiveness (AHR), characteristics of asthmatic attacks. In our preliminary experiments, we evaluated whether ASHMI can also directly modulate ASM contractility/relaxation by studying contractile responses of tracheal segments from BALB/c mice to Ach in the presence and absence of the formula. In this study, tracheal rings harvested from allergic mice 72 hours following the last challenge or naive mice were mounted on a myography apparatus (Multi Myograph Model 610M, DMT-USA, Inc. Atlanta, Ga.) and perfused at 37° C. in oxygenated PSS. Passive tension was applied to the rings and contractility to 60 mM KCL was measured to assess the maximum contractile capacity of each ring (KCL max). After washing, the rings were stimulated with cumulative incremental doses of Ach in the presence or absence of ASHMI, which was added 30 minutes prior to Ach stimulation. Responsiveness to Ach was dramatically and significantly reduced in the presence of the herbal formula. See FIG. 15. Reduction was also seen in rings from naïve and sensitized mice. In both cases, not only was a higher concentration of Ach required to see an initial response, the magnitude of contraction at the maximum dose was reduced by almost 80%. This decreased response was not attributable to loss of viability of the tracheal rings as response to KCL one hour after washout was similar to pre-experiment responses (data not shown). These experiments demonstrate the ability of ASHMI to directly alter airway sensitivity to Ach.

Example 15

T cell Cytokine Gene Expression in the Lung: To determine the role of ASHMI on T cell cytokine responses in lung, we first evaluated cytokine mRNA expression in the lungs using semi-quantitative RT-PCR. Lungs from Ag-challenged, placebo-treated mice showed dramatic increases in IL-4, IL-5 and IL-13, and decreased IFN-γ expression compared with normal controls, demonstrating a Th2-type response. See FIG. 16. In contrast, IL-4, IL-5 and IL-13 mRNA expression in the lungs of ASHMI-treated mice was markedly reduced as compared with placebo-treated mice. IFN-γ mRNA expression in the lungs of ASHMI-treated mice was increased as compared with placebo-treated mice.

Example 16

Figure 17:
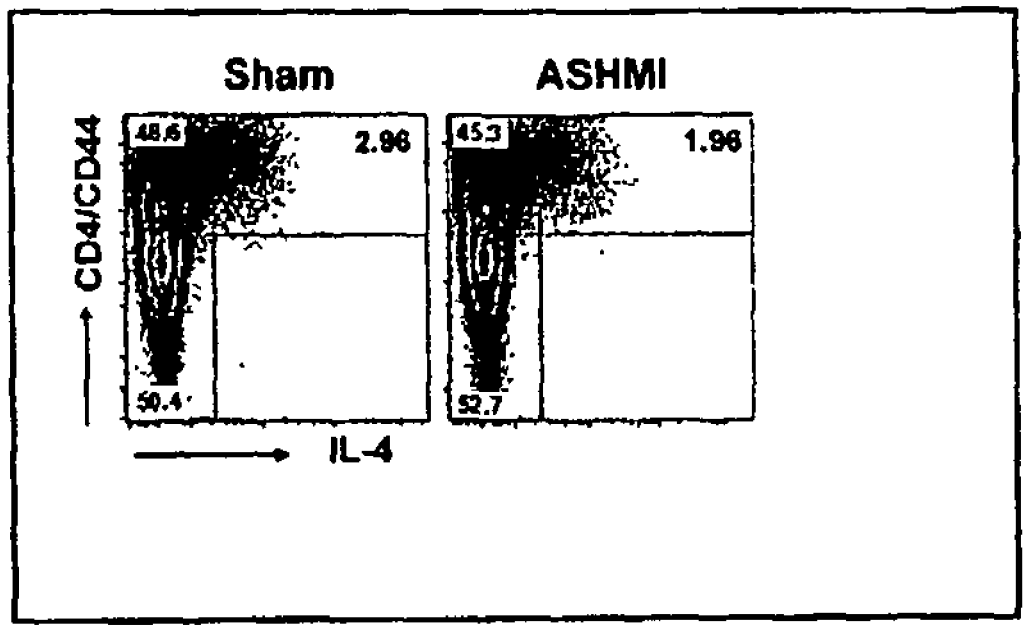
FIG. 17 shows the results of flow cytometry data.

Lung T Cell Response to Recall Antigen Stimulation: To further characterize the effect of ASHMI on T cell responses in lungs of mice with allergic asthma in this model, we isolated cells from left lungs of placebo-treated, ASHMI (normal daily dose) treated, and naïve mice as described previously. We found that the number of lung cells in the ASHMI-treated mice was 5.5 fold less than in placebo-treated mice and were not different from naïve mice ($0.92\times10^6$/per lung). To determine the responses of isolated lung cells to recall antigen stimulation, cells ($1\times10^6$/ml) from each group were cultured with OVA for 48 hours and then with a protein transport inhibitor (Brefaldin A, Sigma) for an additional 6 hours. Cells ($1\times10^6$) were then stained and subjected to flow cytometry analysis. The percent CD4+ IL-4 producing cells in the formula treated group was reduced by 47% as compared with the placebo treated group). No detectable antigen specific CD4+ INF-γ producing cells were detected in any group, but CD8+ IFN-γ producing cells were increased in the ASHMI treated group as compared with the placebo-treated group. There were very few CD8+ IL-4 producing cells in any group (data not shown). These results together with the findings that the present herbal formula suppressed Th2 mRNA levels suggest that formula suppression of Th2 cytokine may be attributed to suppression of CD4 Th2 cytokine producing cells. On the other hand, increased CD8+ IFN-γ producing cells may be linked to the finding that the present ASHMI increased IFN-γ in the lung. Since the present formula reduced lung Th2 cells following recall antigen stimulation, we next determined the effect of the present formula on memory Th2 cells. We found that memory CD4+ IL-4 producing cells (CD3+CD4+CD44+ IL-4+) were also reduced by 44% when compared with the placebo-treated group. See FIG. 17. These results suggest that ASHMI suppresses Th2 effector memory cells, which may contribute to its immunotherapeutic effect on chronic allergic asthma and possible long lasting effect.

Example 17

Th2 Cytokine Secretion by Splenocytes: We determined the role of ASHMI on systemic T cell cytokine secretion. Spleens were collected from placebo-treated, ASHMI-treated, and naïve mice immediately following AHR measurement, and cultured in the presence or absence of OVA. Culture supernatants were harvested 72 hours later and cytokine levels were determined as described in our previous publication. We found that the ASHMI treatment markedly reduced IL-4 as well as IL-5 and IL-13 secretion (data not shown), but did not reduce IFN-γ in cells from the normal daily dose treated group and increased IFN-γ in the half daily dose treated group to recall antigen stimulation as compared to that in placebo-treated group. Interestingly, no significant difference in IFN-γ levels was observed between ASHMI treated and placebo-treated groups following Con A mitogen stimulation. These results suggest that ASHMI modulates T cells in an antigen-specific manner.

Example 18

Figure 18:
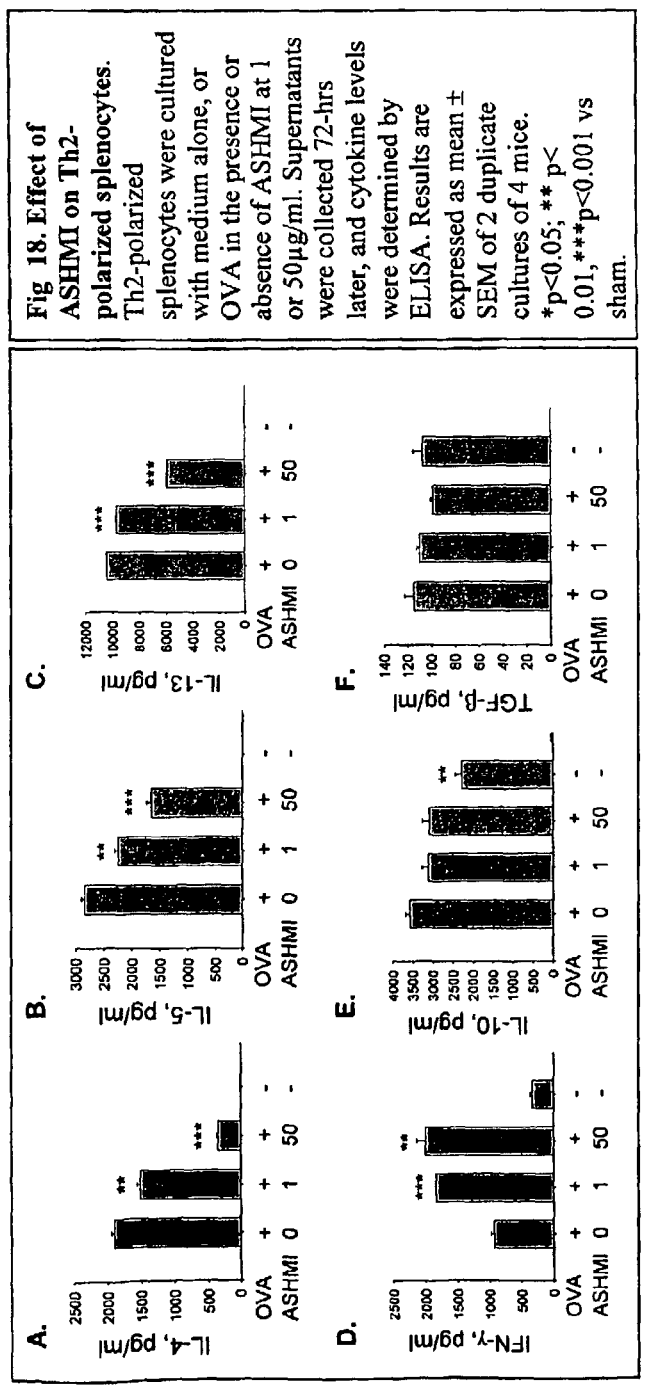
FIG. 18 shows the effect of ASHMI on Th2-polarized splenocytes.

SPCs Responses to Antigen Stimulation: We also determined whether ASHMI could modulate Th2 polarized response in vitro. Splenocytes, isolated from the mice with allergic airway responses following OVA sensitization and challenges as described above, were cultured in the presence and absence of OVA with or without ASHMI. We found that the antigen primed SPCs produced Th2 cytokines IL-4, IL-5 and IL-13 to recall antigen stimulation and IL-13 production reached 11,000 pg/ml while there was a slight increase in IFN-γ as compared with that of naïve SPCs, suggesting a dominant Th2-polarized response. ASHMI significantly suppressed all major Th2 cytokines, IL-4, IL-5 and IL-13, and increased IFN-γ production. Furthermore, a dose response was observed. See FIG. 18. We previously found that the original formula MSSM-002 at 50 μg/ml was effective in suppression of Th2 cytokines and increasing IFN-γ. IL-10, a classical Th2 cytokine, which suppressed IFN-γ and IL-12 secretion, has been recently suggested to exhibit suppression of allergic inflammation. We, therefore, also determine the IL-10 levels. However, we found that ASHMI suppressed IL-10 production, suggesting that IL-10 is unlikely to play an important role in mediating ASHMI-based therapeutic effects. Other recent studies also found that decreased IL-10 rather than increased IL-10 was associated with reduced AHR and reduced Th2 responses. TGF-β levels were not different between formula treated and untreated OVA stimulated cultures. These results suggest that ASHMI was able to modulate the polarized Th2 responses by SPCs and its potency was essentially the same as the original formula MSSM-002.

Example 19

Figure 19:
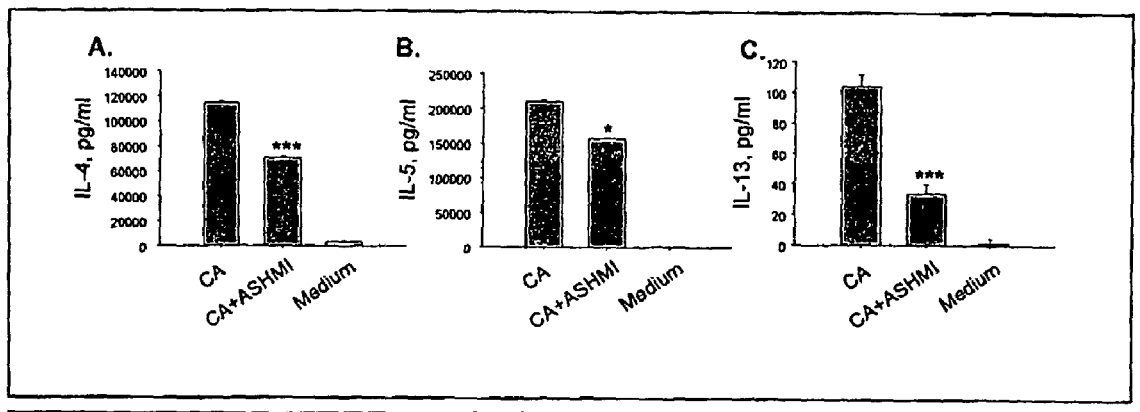
FIG. 19 shows the effect of ASHMI on D10 cells.

Suppression of Th2 Cytokine Synthesis by the Long Term Committed Th2 Clone, D10 Cells: Although Th2 polarized SPCs within a mixed cell population mimic physiological conditions, the long term committed Th2 cell line provides a tool to determine the direct effect of ASHMI on Th2 cells. To determine whether ASHMI can directly suppress Th2 cell activities we used Th2 clone, D10 cells, a well-characterized CA-specific Th2 clone generated from AKR mice as an in vitro model. D10 cells that produce high levels of Th2 cytokines, but virtually no IFN-γ, do not respond to IL-12 due to lack of IL-12β2 receptors. Many studies used these cells to characterize the role of Th2 cells in the pathogenesis of allergic reactions and to test various approaches to modulation of the Th2 phenotype. As found with SPCs, ASHMI significantly suppressed IL-4, IL-5, and IL-13 production by D10 cells. See FIG. 19. These results are consistent with our previous finding that the original formula MSSM-002 suppression of polarized Th2 cells is IL-12 independent, quite different from the adjuvant induced effect on T cells.

Example 20

Figure 20:
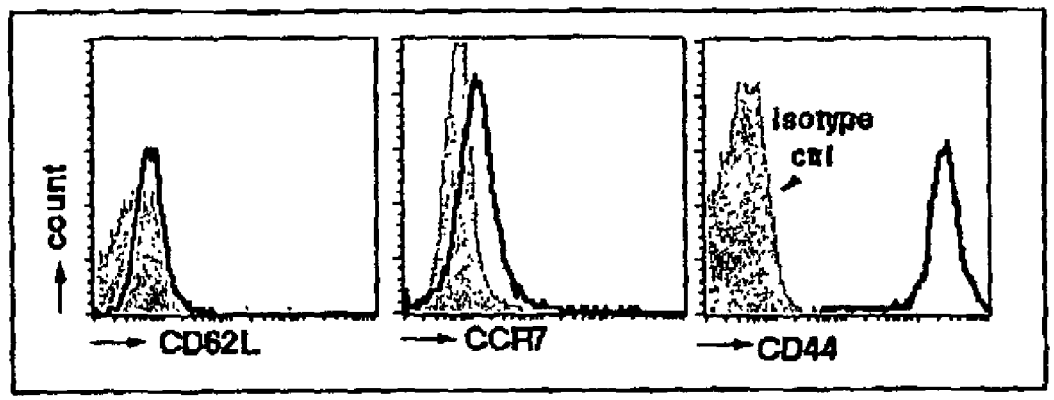
FIG. 20 depicts the phenotype of the Th2 polarized cell line, D10.G4.1.

Phenotype of D10 cells: As shown in our previous studies, D10 cells can function as effector memory Th2 cells. In order to establish a protocol for identification of murine effector memory Th2 cells from lung, we used D10 cells and Fc-CCL19 (CCR7 ligand) fusion protein (from Dr. Cyster's laboratory in UCSF, Calif.) as previously described. Resting D10 cells were stimulated with anti-CD3 for 3 days. To detect CCR7 cell surface expression, cells were incubated with Fc-block (anti-CD16/CD32) and then with additional diluted Fc-CCL19 and incubated on ice for 30 minutes. Normal human IgG was used as isotype control. After washing biotin labeled anti-human Fc (Jackson ImmunoReseach, West Grove, Pa.) was added. Then the cells were labeled with streptavidin-PerCp (Jackson ImmunoResearch, West Grove, Pa.), FITC-conjugated anti-CD62L, and APC-conjugated anti-CD44 (eBioscience, San Diego, Calif.). Cells were analyzed by FACS Calibur and Cellquest software (BD Bioscience, San Jose, Calif.). The result shows that in D10 cells the expression of CD44 (memory murine T cell marker) is high and homing receptors, CD62L and CCR7 are negative, demonstrating the phenotype of effector memory cells. See FIG. 20. We will use this method to identify and quantitate the effect of treatment with ASHMI on effector lung memory T cells.

Example 21

Figure 21:
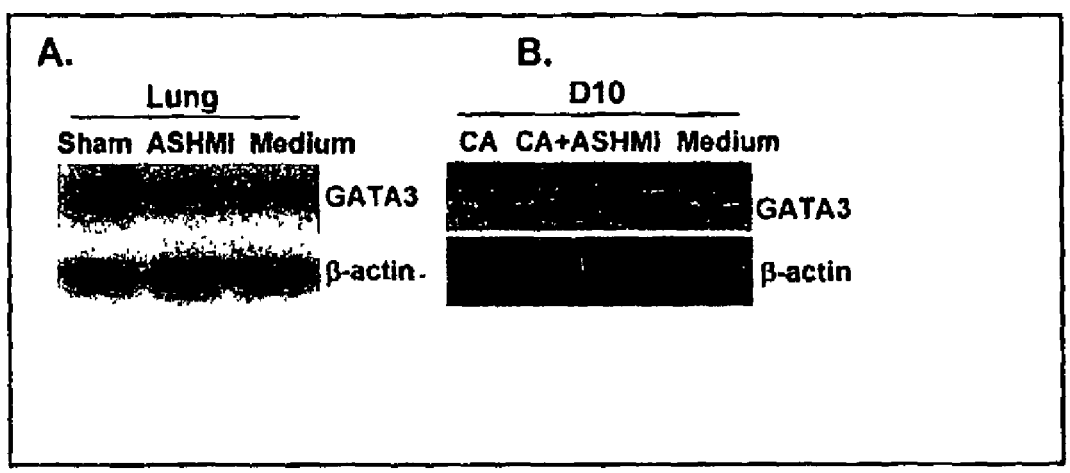
FIG. 21 depicts the Western blot analysis to determine GATA-3 protein expression in lung tissue and D10 cells.
Figure 22:
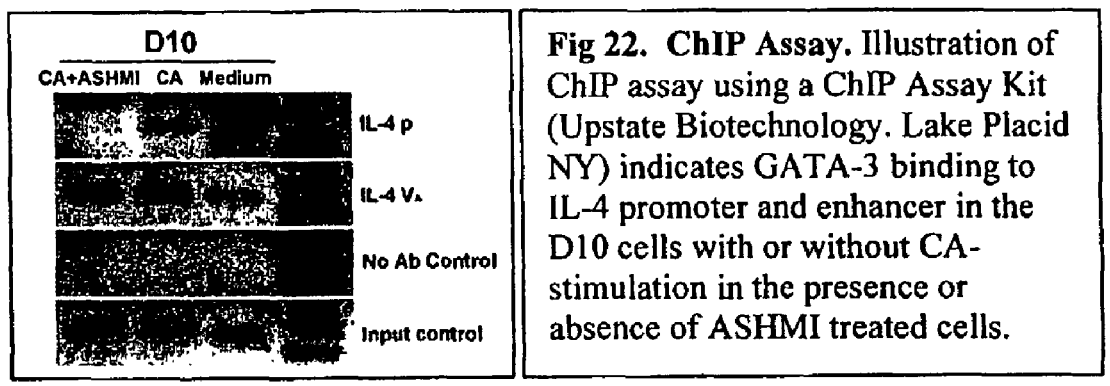
FIG. 22 illustrates the ChIP assay for indicating GATA-3 binding to IL-4 promoter and enhancer in the D10 cells.

Suppression of GATA-3 Production: Since ASHMI directly suppressed Th2 cytokine synthesis in a non-toxic manner, we hypothesized that ASHMI may directly suppress Th2 transcription factors, as observed with our original formula. Because GATA-3 determines Th2 cell commitment and memory, and ASHMI suppressed Th2 polarized cells in the lung, we determined the effect of ASHMI on GATA-3 protein synthesis in the lung. The middle lobes of the lungs were harvested from placebo-treated, ASHMI-treated (normal daily dose), or naïve mice. GATA-3 protein content was determined by western blotting. We found that GATA-3 content in the lung of ASHMI treated mice was reduced as compared with lungs of placebo treated mice, suggesting that ASHMI suppression of Th2 polarized cells may be due to its effect on GATA-3 production. To provide direct evidence that ASHMI suppressed GATA-3 in Th2 polarized cells, D10 cells were cultured with or without CA in the presence or absence of ASHMI. After harvesting supernatants, cells were harvested and subjected to the Western blotting. We found that GATA-3 content in ASHMI treated cells was also reduced. See FIG. 21. Because D10 cells are a well characterized Th2 clone widely used in previous studies of Th2 cell regulatory mechanisms, they provided us with a critical tool for further investigation of the mechanisms of ASHMI-down-regulation of GATA-3 and Th2 cytokines. See FIG. 22.

Example 22

IL-4 Gene Transactivation: IL-4 is a key Th2 cytokine and previous studies showed that GATA-3 directed IL-4 gene activity involves regulation of both IL-4 promoter and enhancer regions. Therefore, to further understand the molecular mechanism underlying ASHMI modulation of GATA-3 associated Th2 cytokine expression, we compared GATA-3 binding to IL-4 promoter and enhancer regions in ASHMI-treated and untreated-D10 cells. Although binding of GATA-3 to both IL-4 promoter and enhancer regions in CA-stimulated D10 cells was observed, there was virtually no binding of GATA-3 to IL-4 promoter and reduced binding to IL-4 enhancer regions in the ASHMI-treated, CA stimulated-D10 cells. These findings suggest that ASHMI suppresses GATA-3 binding to the regulatory sequences of IL-4 gene resulting in down-regulation of IL-4 expression.

Example 23

Summary: In this preliminary study, we demonstrated that ASHMI has a broad spectrum of actions on allergic airway responses in the murine model of allergic asthma as evidenced by abrogation of antigen-induced AHR and marked reduction of pulmonary inflammation and significant reduction of Th2 responses (Th2-cytokines and IgE). We also found that ASHMI has a large therapeutic safety window. Furthermore, ASHMI inhibited airway remodeling in the model of chronic asthma, and reduced ASM contractile response to Ach. All of these actions would benefit asthma patients. This preliminary study demonstrated that ASHMI suppression of Th2 polarized cells is associated with down regulation of the Th2 transcription factor GATA-3. Because of its efficacy, safety as tested in the current protocol, and relative simplicity of the herbal composition, ASHMI will be further investigated as a Chinese herbal therapy for treating asthma in our murine models. We will further explore the molecular and cellular mechanisms of ASHMI immunomodulation of T cells.

Example 24

Clinical Effect of CHT in Human Asthma: In our study, we examined the effect of ASHMI on allergen-stimulated peripheral blood mononuclear cells (PBMCs) from patients with asthma and dust mite or peanut allergy. As seen in the studies of murine splenocytes and T cells from milk-specific T-cell lines treated with MSSM-002, ASHMI significantly decreased IL-5 production by PBMCs from 7 allergic asthmatic patients but did not significantly affect the production of interferon-Y. This beneficial immunoregulatory effect and the findings of a broad spectrum actions of ASHMI on allergic asthma pathogenesis in the murine model of chronic asthma, the safety data, as well as the history of clinical use of individual components in ASHMI lead us to hypothesize that ASHMI will be safe and effective in improving the outcome of asthma in atopic patients with moderate—severe, persistent asthma.

Mice and Reagents: Male AKR/J mice (6 weeks old) purchased from the Jackson Laboratory (Bar Harbor, Me.) were maintained in the animal facility at Mount Sinai School of Medicine. Standard guidelines for lab animal care were followed (Fahy et al. "The effect of an anti-IgE monoclonal antibody on the early- and late-phase response to allergen inhalation in asthmatic subjects [see comments]" Am. J. Respir. Crit. Care Med. 155:1828-1834, 1997; incorporated herein by reference). Conalbumin (CA), Concanavalin A (Con A), Dex, and dinitrophenyl conjugated with albumin (DNP-albumin) were purchased from Sigma (St. Louis, Mo.). Antibodies for ELISAs were purchased from the Binding Site Inc. and PharMingen (San Diego, Calif.). Anti-DNP IgE and IgG2a were purchased from Accurate Scientific Inc. (New York).

Composition Formulation: Both MSSM-001 and MSSM-002 were formulated according to the standard preparation protocol for decoctions (Bensky et al., Chinese Herbal Medicine Formulas & Strategies. Eastland Press, 1999). MSSM-001 was based on a preparation used by one of the present inventors to treat asthma and bronchitis in children in the Pediatric Department of the China Japan Friendship Hospital.

Antigen (AG)-Sensitization/Challenge and MSSM-002 Treatment: Mice (AKR 6 Week old, n 8) were injected twice (on days 0 and 7) i.p. with CA (200 µg) in alum (2 mg) followed by 3 i.t administrations (on days 14, 24, and 34). Mice were treated twice daily with MSSM-002 (270 mg/mouse) intragastrically (ig) starting 24 hours after the first i.t. administration for 18 consecutive days. Intragastric feeding was performed by means of a 25-gauge stainless steel blunt feeding needle (Fine Science Tool Inc, CA, USA). The dose of herbal formula used in this study was based on the equivalent effective dose by weight prescribed for humans (Xiu "The experimental method of pharmacology" Beijing: The People's Public Health Publisher 985-924, 1986; incorporated herein by reference). Dexamethasone-treated mice received 0.5 mg/kg/day i.p. daily, as described previously (De et al. "Effect of dexamethasone and endogenous corticosterone on airway hyperresponsiveness and eosinophilia in the mouse" Br. J. Pharmacol. 119:1484-1490, 1996; incorporated herein by reference). Placebo treated mice received saline ig daily. Naive mice served as additional controls.

Measurement of Late-Phase Airway Responses: Three days after the last i.t. Ag challenge, airway responsiveness was determined by measuring airway pressure changes following iv acetylcholine injection as previously described (Li et al. "Induction of pulmonary allergic responses by antigen-specific Th2 cells" J. Immunol. 160:1378-1384, 1998; Li et al. "Mucosal IFN-gamma gene transfer inhibits pulmonary allergic responses in mice" J. Immunol. 157:3216-3219, 1996; Levitt et al. "Expression of airway hyperreactivity to acetylcholine as a simple autosomal recessive trait in mice" FASEB J. 2:2605-2608, 1988; each of which is incorporated herein by reference). Mice were anesthetized with sodium pentobarbital (80 mg/kg) and ventilated via a tracheal cannula (18 gauge) at the rate of 120 breaths/minute and a constant tidal volume of air (0.2 ml) with RSP1002 Pressure Controlled Respirator System (Kent Scientific Corporation, CT). Muscle paralysis was induced by iv injection of decamethonium bromide (25 mg/kg). Airway pressure was measured with a pressure transducer via a port in the trachea. Two minutes after establishing a stable airway pressure recording, acetylcholine was injected iv (50 µg/kg). The airway pressure changes were viewed and recorded, using the VENTP software respiratory data acquisition system (Kent Scientific Corporation, CT). The time-integrated changes in peak airway pressure referred to as the airway pressure-time index (APTI; cm H2O per second) was calculated and served as the measurements of airway responsiveness.

Measurement of Serum CA Specific Antibodies: Blood was obtained from each group of mice immediately following APTI measurements. After centrifugation, the sera were collected and stored at −80° C. CA-specific IgE levels were measured by ELISA as described previously (Li et al. "Induction of pulmonary allergic responses by antigen-specific Th2 cells" J. Immunol. 160:1378-1384, 1998; incorporated herein by reference). For measurement of CA-specific IgG2a, plates were coated with CA and then were blocked and washed as above. Samples (1:50 dilution) were added to the plates and incubated overnight at 4° C. Plates were washed, and biotinylated rat anti-mouse IgG2a monoclonal antibodies were added. Plates were incubated for an additional 45 minutes at RT. After washing, avidin-peroxidase (Sigma, 1:1000 dilution) was added for an additional 15 minutes at ambient temperature. After eight washings, the reactions were developed with ABTS (KPL) for 30 min. at RT and read at 405 nm.

Levels of antigen-specific IgE and IgG2a were calculated by comparison with a reference curve generated by using mouse monoclonal antibodies, anti-DNP IgE or IgG2 (Accurate Scientific Inc., NY, USA), as described previously (Li et al. "Induction of pulmonary allergic responses by antigen-specific Th2 cells" J. Immunol. 160:1378-1384, 1998; incorporated herein by reference). Briefly, DNP-albumin was coated at the same concentration as CA. After overnight incubation at 4° C., the plates were washed and blocked as described above. Ten serial 1:2 dilutions of mouse anti-DNP IgE or IgG2a antibodies starting from 1000 ng/ml were added. Thereafter all the steps were performed in a similar manner as above. All analyses were performed in duplicate and coefficient of variation (CV)>15% repeated to ensure a high degree of precision.

Cell culture and quantification of cytokines: Immediately following APTI measurement, spleen cells were isolated and suspended in complete culture medium (RPMI 1640 containing 10% fetal bovine serum, 1% penicillin/streptomycin, and 1% glutamine). Cells (4×106/ml/well) were cultured in 24 well plates in the presence or absence of CA (50 µg/ml) or Con A (2 µg/ml). Supernatants were collected after 72-hour culture.

Levels of IL-4, IL-5, IL-13, and IFN-γ in spleen culture supernatants were determined by ELISA according to the manufacturer's instructions (PharMingen, San Diego), as previously described (Li et al. "Induction of pulmonary allergic responses by antigen-specific Th2 cells" J. Immunol. 160:1378-1384, 1998; incorporated herein by reference).

Example 25

Safety Testing of ASHMI: Each herb in ASHMI, Ling-Zhi (Ganodenna lucidum) Ku-Shen (Radix Sophorae Flavescentis) and Gan-Cao (Radix Glycyrrhizae), is a lawfully prescribed herbal medicine in China and the United States and is safe when used alone or in combinations in the traditionally prescribed manner. The doses of individual herbs in ASHMI used in our studies are within the range prescribed by the Pharmacopoeia of the Peoples Republic of China. The results of a thorough search of English and Chinese scientific literature revealed no reports of toxicity attributable to therapeutic use of these 3 herbs. To further ensure the safety of the formula, we tested acute toxicity—lethality (single dose, LD 50). In our preliminary testing, no animal died after feeding 25 times (225 mg, the maximal dose we can administer to mice) the normal daily dose used, as described above. We monitored those mice for an additional 2 weeks. All mice appeared healthy. No abnormalities of major organs were detected by histological analysis. To further assess safety under therapeutic does and course (multiple doses, sub chronic toxicity), blood and sera were obtained from mice following 6 weeks treatment with ASHMI, or water (placebo treatment) and naïve mice. The animals were subjected to complete blood test (CBC) and biochemical analysis of liver and kidney functions using PROCHEM-V instrumentation (Synbiotics Company, New Jersey) by the Mount Sinai School of Medicine, Center for Laboratory Animal Sciences, where these assays are routinely performed to monitor the health of laboratory animals. All the results were within the normal range, as set forth below in Table 7.

TABLE 7

Biochemical analysis of liver and kidney functions

|  | Placebo | MS3D ½X | MS3D 1X | Naïve | Reference Range |
|---|---|---|---|---|---|
| BUN | 19 ± 2 | 22 ± 5 | 20 ± 0 | 21 ± 1 | 9-36 mg/dL |
| ALT | 55 ± 5 | 68 ± 4 | 52 ± 4 | 33 ± 7 | 22-400 mg/dL |

N = 6-8

Example 26

Assessment of Individual Herb Components: Each of the individual herb components of ASHMI was subjected to the certain assays as described above. Specifically, each of the individual herbs was dosed according to the protocol described above and the results of each assay are summarized below.

Figure 23:
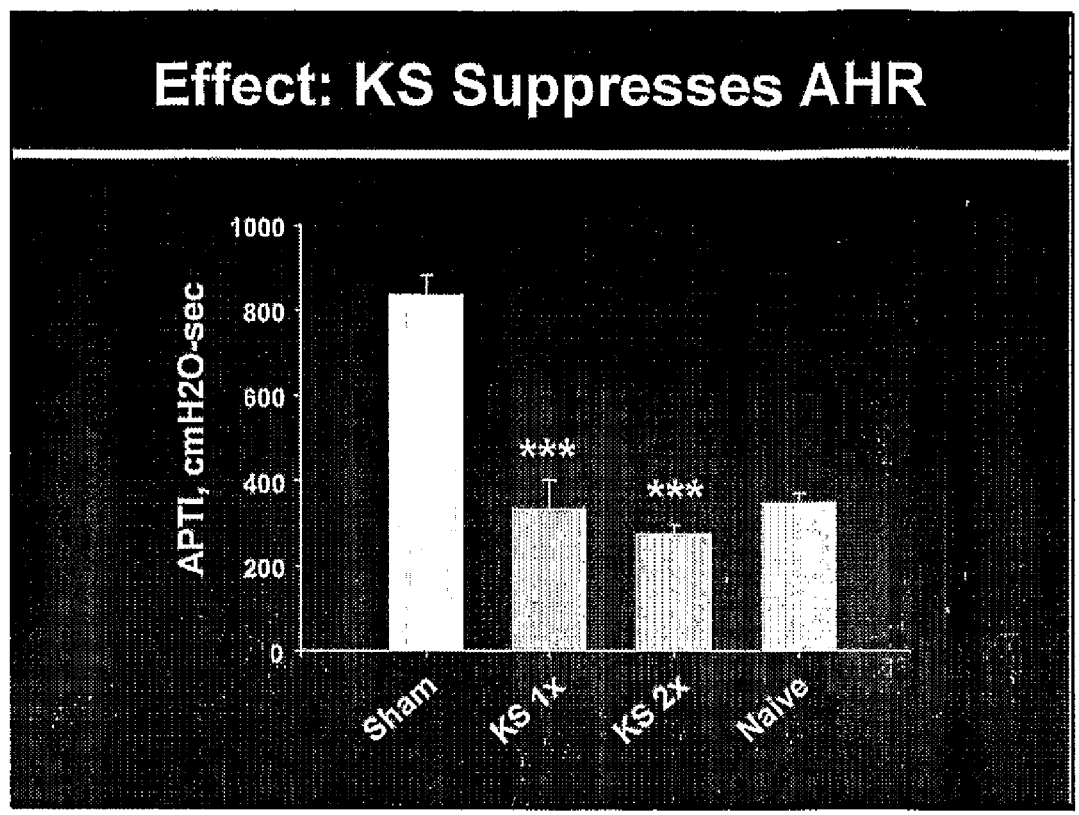
FIG. 23 shows the effect of Ku-Shen on AHR.

Effect of Ku-Shen on AHR: Results were obtained by methods substantially similar to those described herein and are set forth in FIG. 23.

Figure 24:
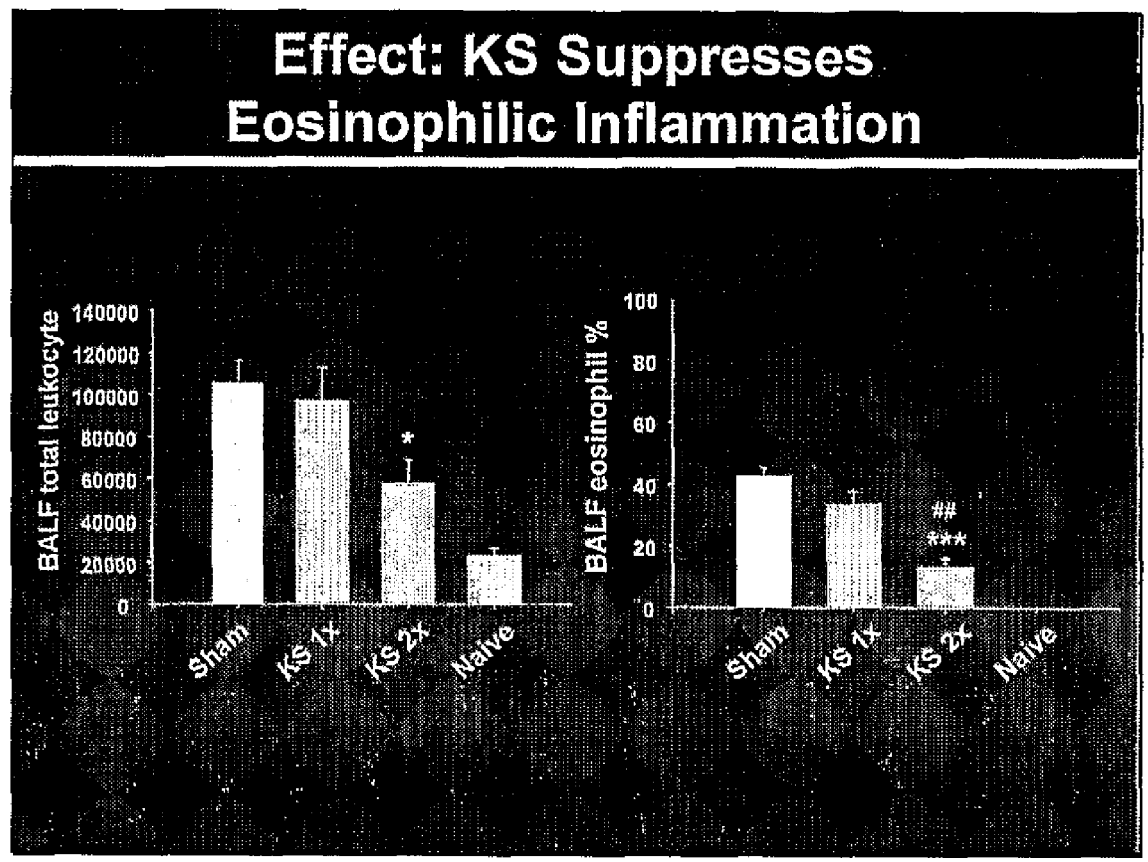
FIG. 24 shows the effect of Ku-Shen on eosinophilic inflammation.

Effect of Ku-Shen on Eosinophilic Inflammation: Results were obtained by methods substantially similar to those described herein and are set forth in FIG. 24.

Figure 25:
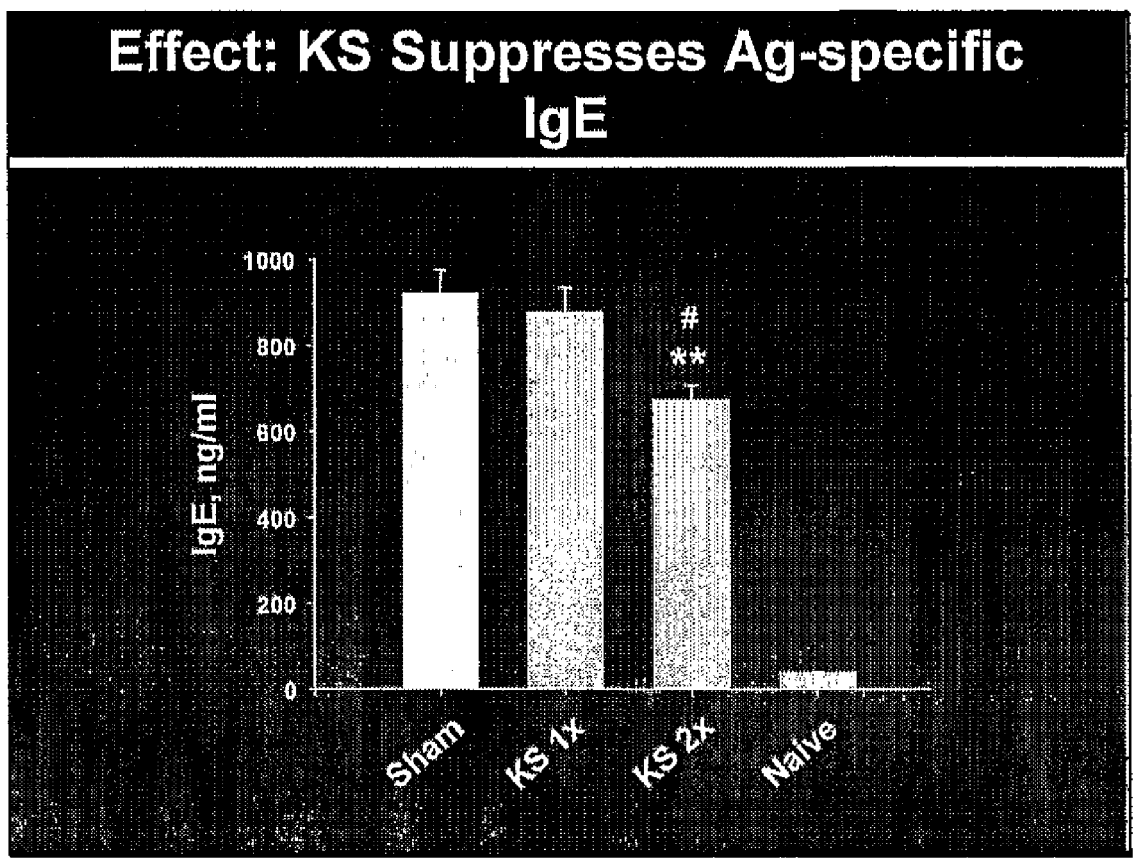
FIG. 25 shows the effect of Ku-Shen on Ag-specific IgE.

Effect of Ku-Shen on Ag-Specific IgE: Results were obtained by methods substantially similar to those described herein and are set forth in FIG. 25.

Figure 26:
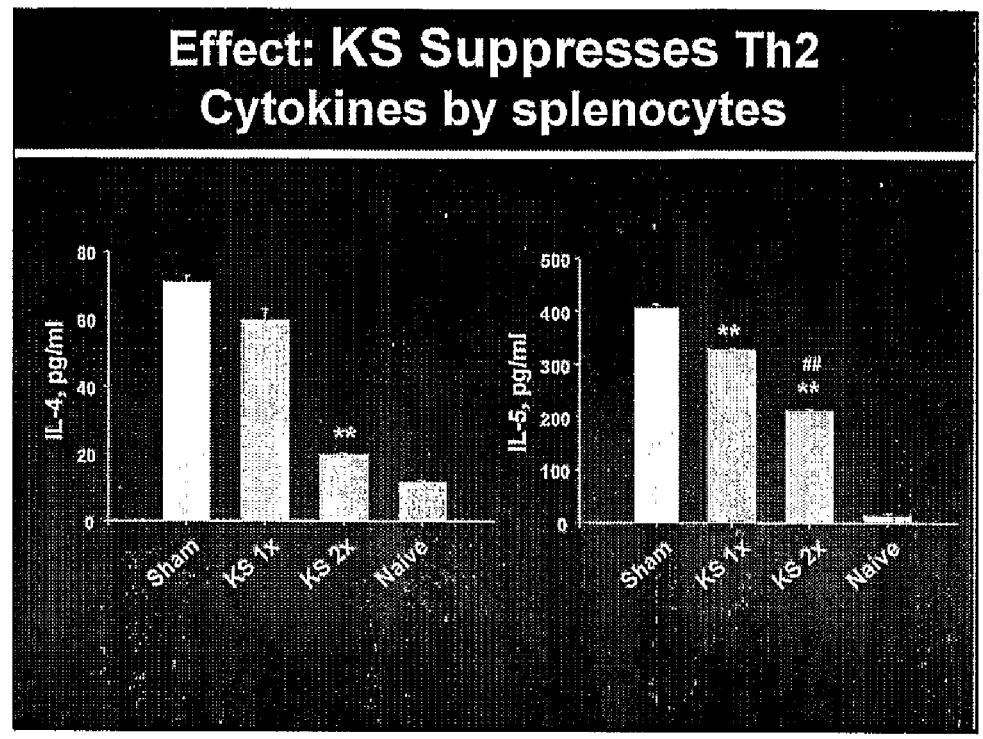
FIG. 26 shows the effect of Ku-Shen on Th2 cytokines.

Effect of Ku-Shen on Th2 Cytokines by Spleenocytes: Results were obtained by methods substantially similar to those described herein and are set forth in FIG. 26.

Figure 27:
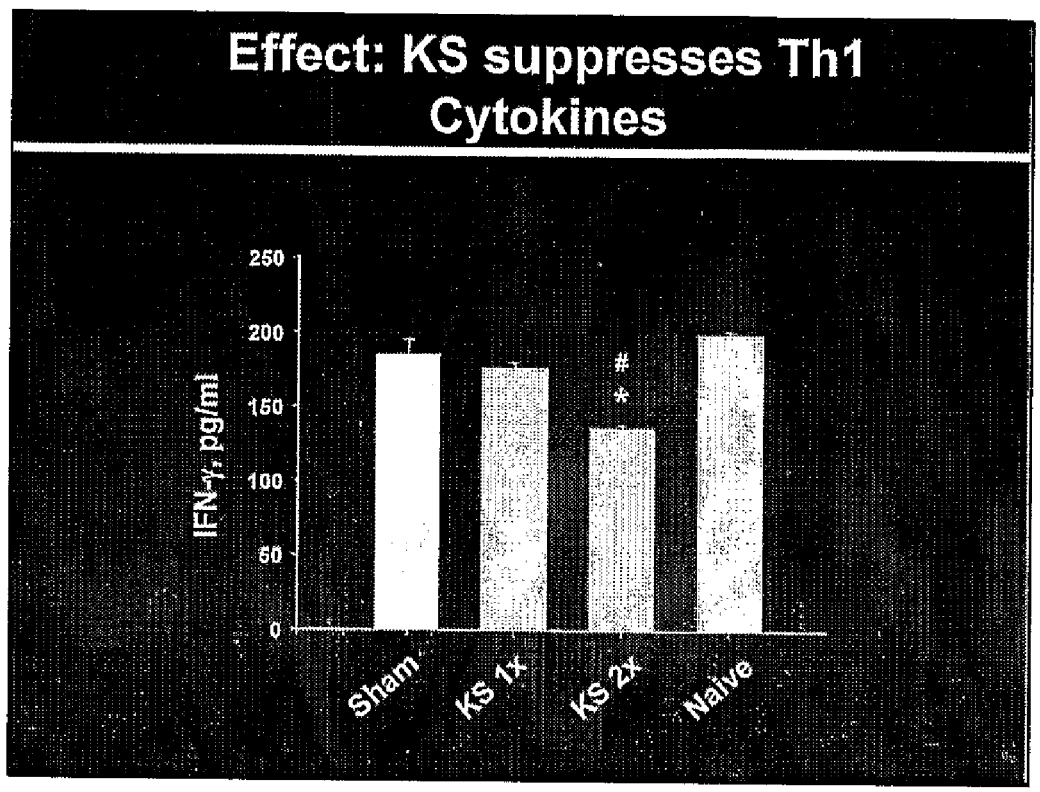
FIG. 27 shows the effect of Ku-Shen on Th1 cytokines.

Effect of Ku-Shen on Th1 Cytokines: Results were obtained by methods substantially similar to those described herein and are set forth in FIG. 27.

Multiple Dose Effects of Ku-Shen on Liver and Kidney Function: Results were obtained by methods substantially similar to those described herein and are set forth in Table 8, below.

TABLE 8

Biochemical analysis of liver and kidney functions

|  | Sham | Ku-Shen | Naïve | Reference Range |
|---|---|---|---|---|
| BUN | 19 ± 2 | 18 ± 1 | 21 ± 1 | 9-36 mg/dL |
| ALT | 55 ± 5 | 50 ± 5 | 33 ± 7 | 22-400 mg/dL |

Figure 28:
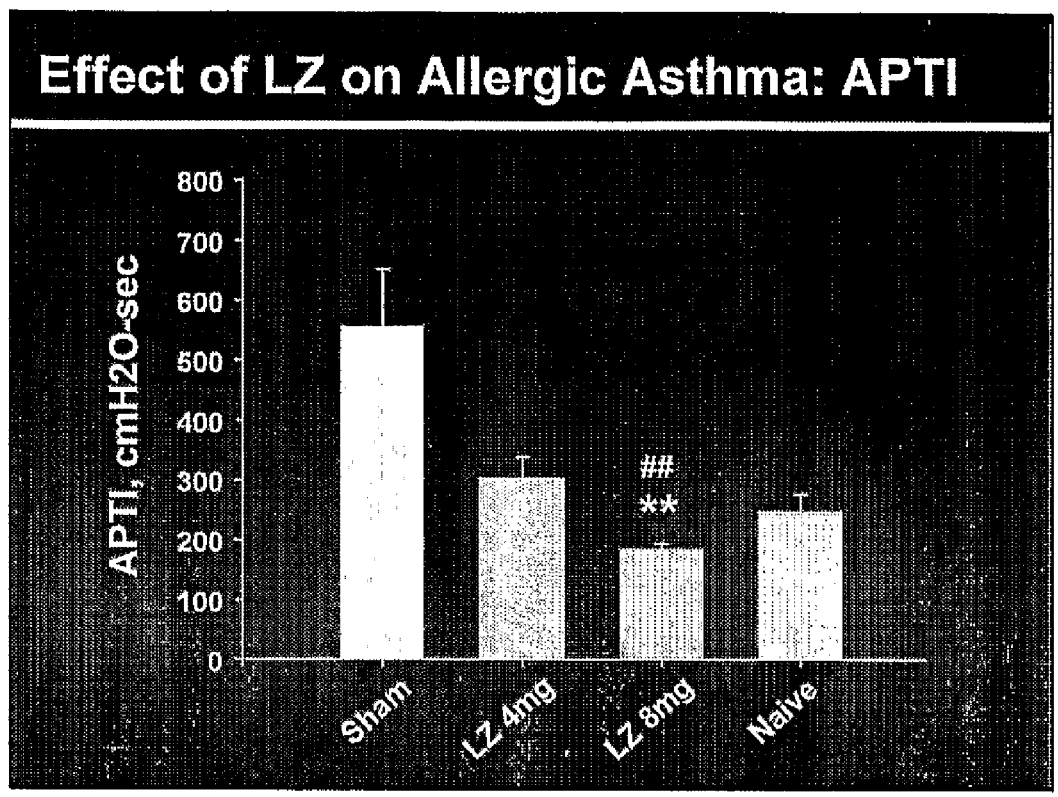
FIG. 28 shows the effect of Ling-Zhi on allergic asthma ATPI.

Effect of Ling-Zhi on Allergic Asthma ATPI: Results were obtained by methods substantially similar to those described herein and are set forth in FIG. 28.

Figure 29:
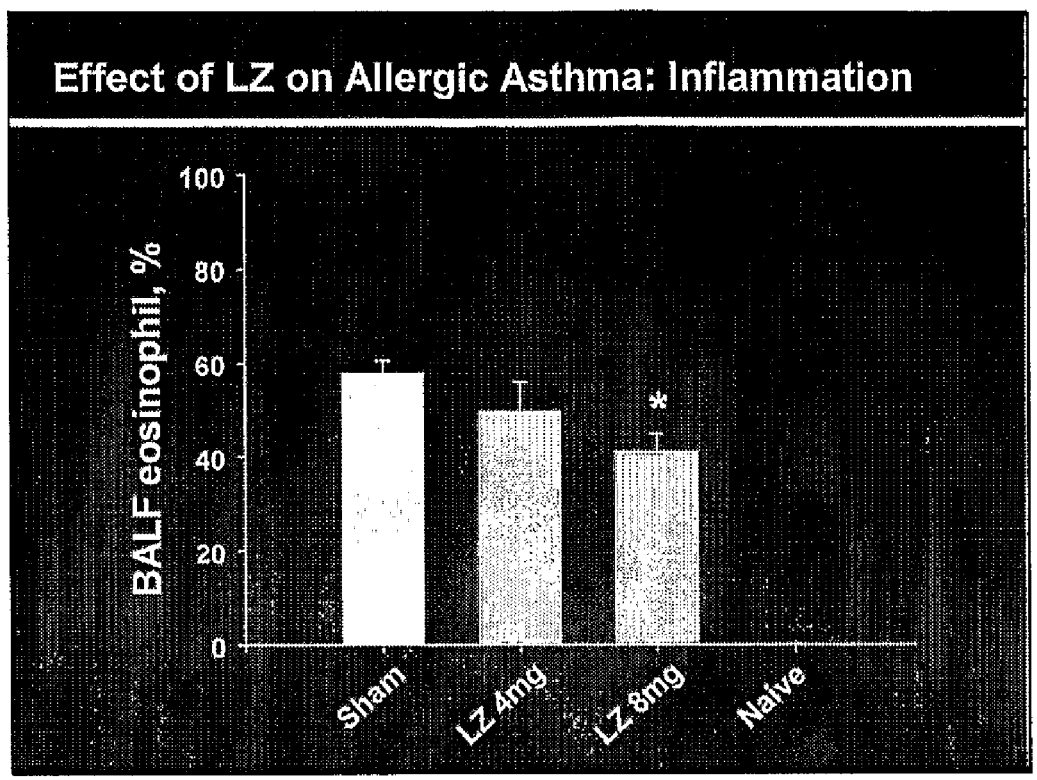
FIG. 29 shows the effect of Ling-Zhi on eosinophilic inflammation.

Effect of Ling-Zhi on Eosinophilic Inflammation: Results were obtained by methods substantially similar to those described herein and are set forth in FIG. 29.

Figure 30:
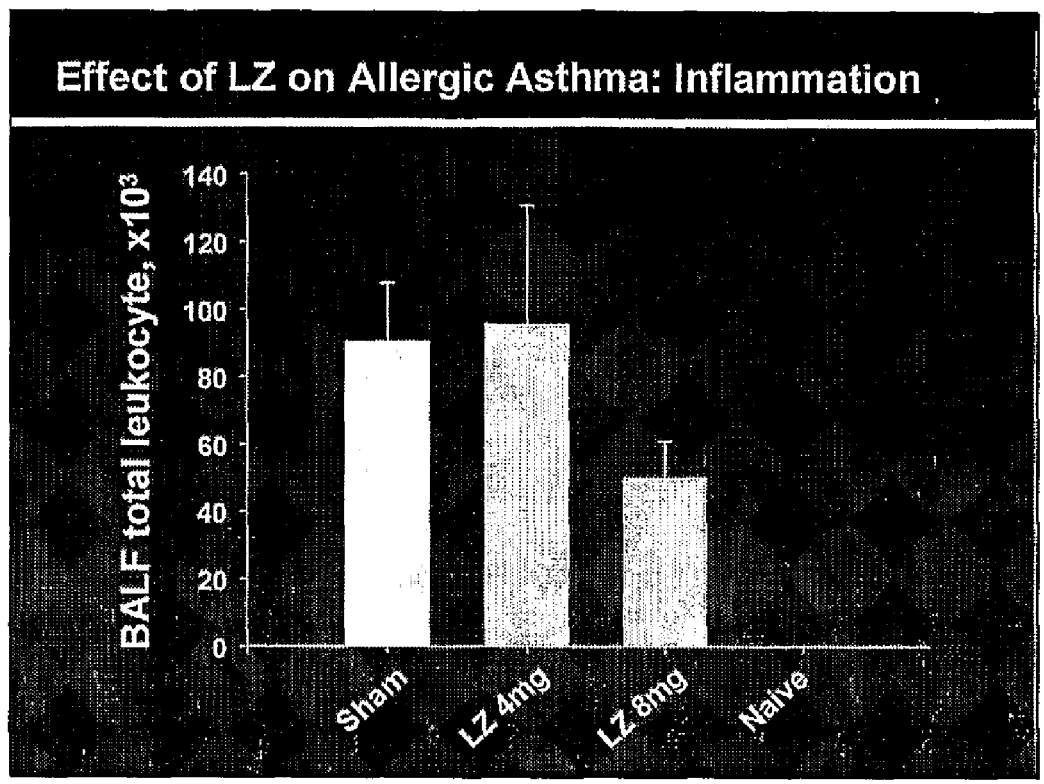
FIG. 30 shows the effect of Ling-Zhi on leukocyte inflammation.

Effect of Ling-Zhi on Leukocyte Inflammation: Results were obtained by methods substantially similar to those described herein and are set forth in FIG. 30.

Figure 31:
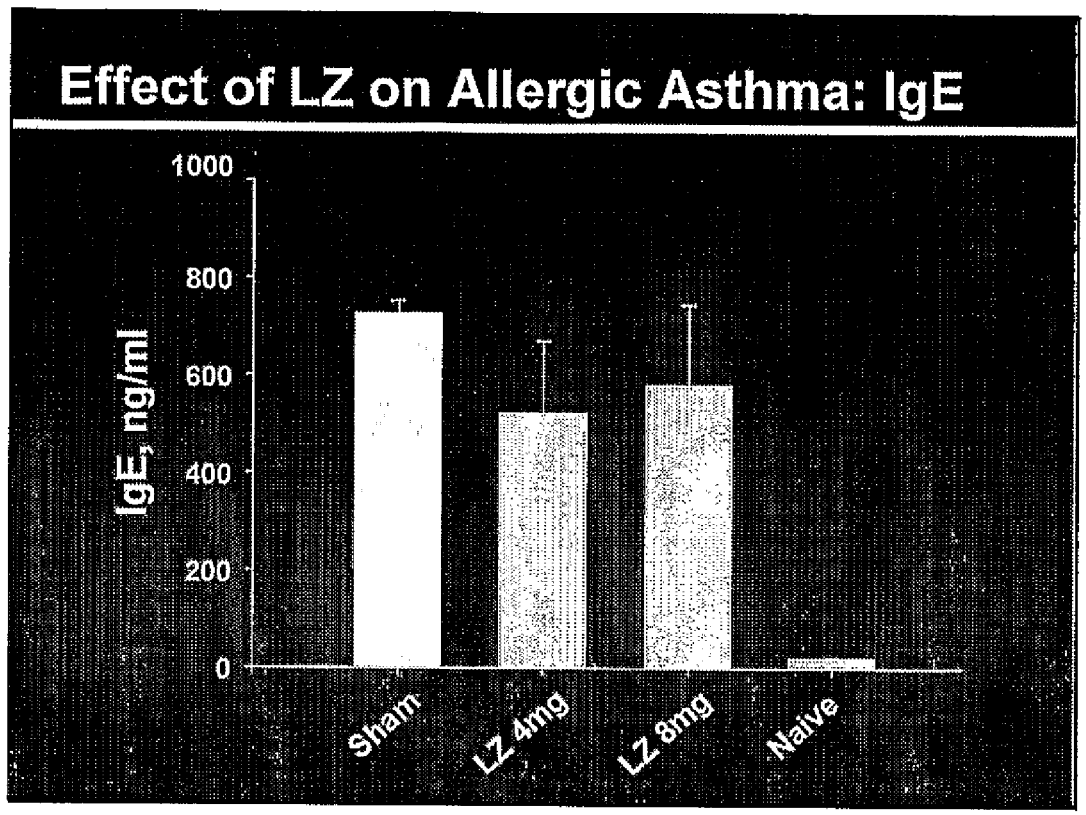
FIG. 31 shows the effect of Ling-Zhi on IgE.

Effect of Ling-Zhi on IgE: Results were obtained by methods substantially similar to those described herein and are set forth in FIG. 31.

Figure 32:
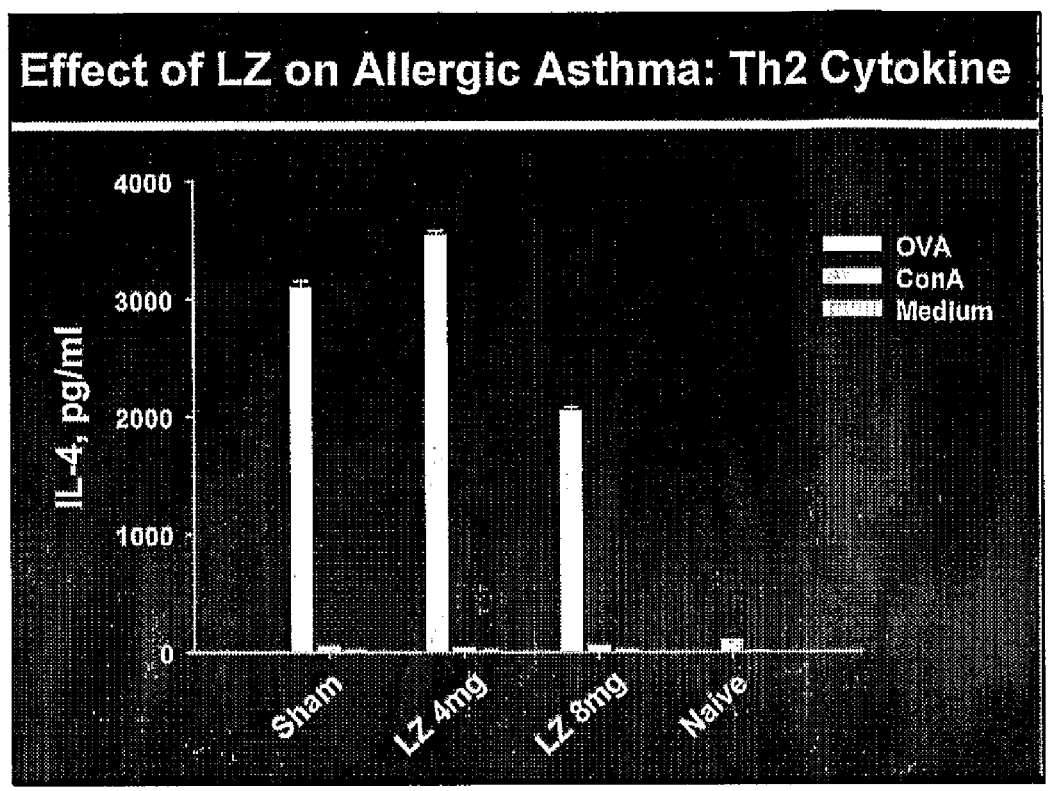
FIG. 32 shows the effect of Ling-Zhi on Th2 cytokines.

Effect of Ling-Zhi on Th2 Cytokines: Results were obtained by methods substantially similar to those described herein and are set forth in FIG. 32.

Figure 33:
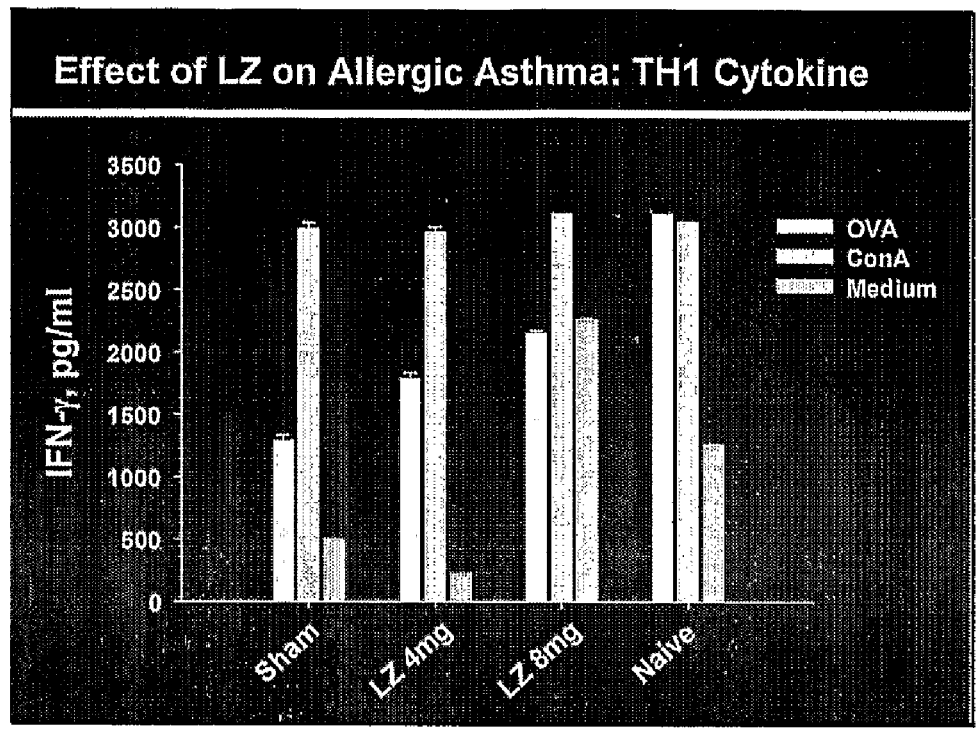
FIG. 33 shows the effect of Ling-Zhi on Th1 cytokines.

Effect of Ling-Zhi on Th1 Cytokines: Results were obtained by methods substantially similar to those described herein and are set forth in FIG. 33.

Effect of Ling-Zhi on Kidney and Liver Function: Results were obtained by methods substantially similar to those described herein and are set forth in Table 9, below.

TABLE 9

Biochemical analysis of liver and kidney functions

|  | Sham | Ling-Zhi | Naïve | Reference Range |
|---|---|---|---|---|
| BUN | 19 ± 2 | 22 ± 2 | 21 ± 1 | 9-36 mg/dL |
| ALT | 55 ± 5 | 83 ± 20 | 33 ± 7 | 22-400 mg/dL |

Figure 34:
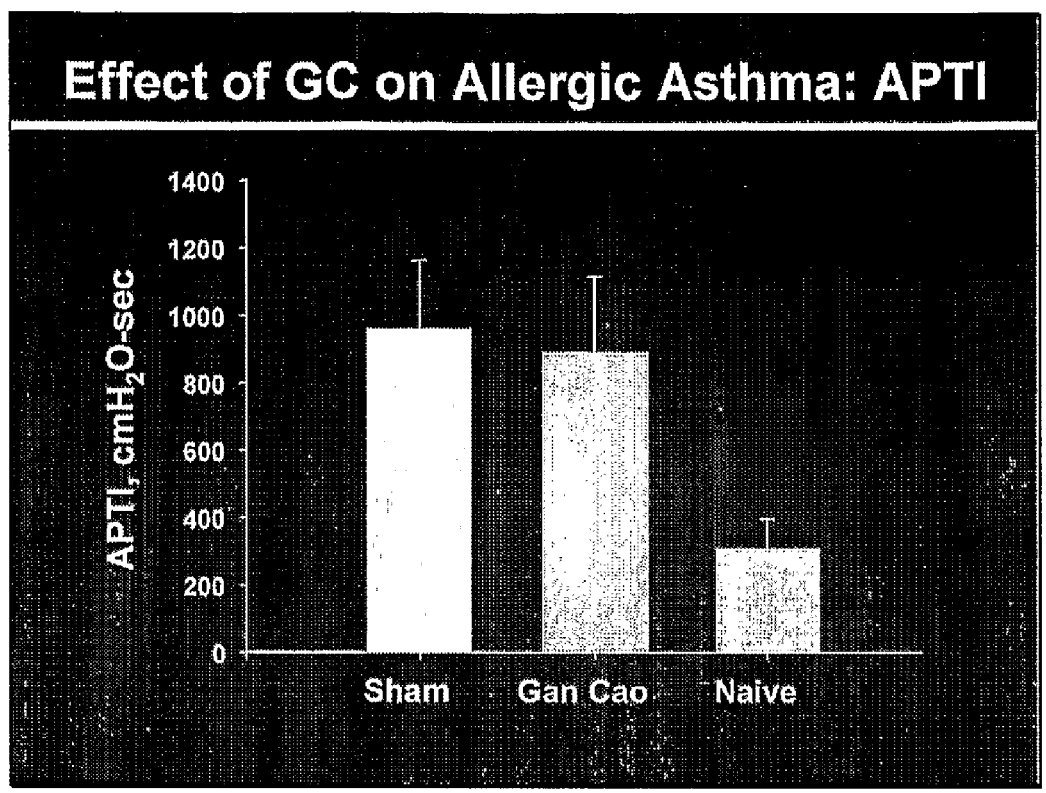
FIG. 34 shows the effect of Gan-Cao on allergic asthma ATPI.

Effect of Gan-Cao on Allergic Asthma ATPI: Results were obtained by methods substantially similar to those described herein and are set forth in FIG. 34.

Figure 35:
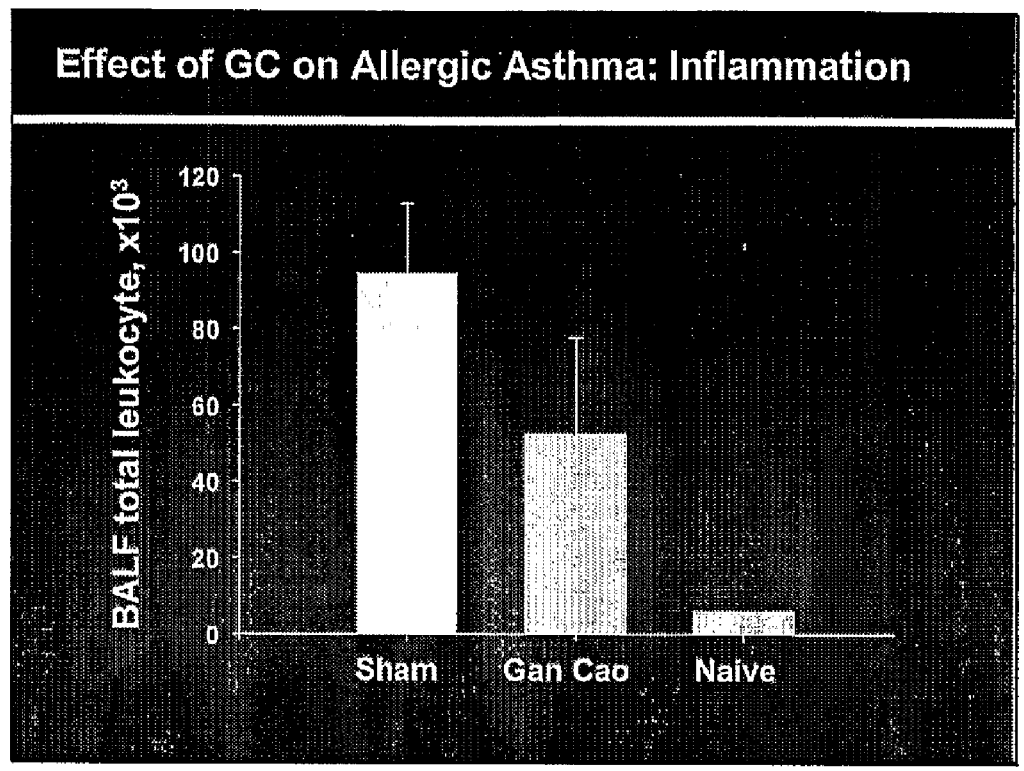
FIG. 35 shows the effect of Gan-Cao on leukocyte inflammation.

Effect of Gan-Cao on Leukocyte Inflammation: Results were obtained by methods substantially similar to those described herein and are set forth in FIG. 35.

Figure 36:
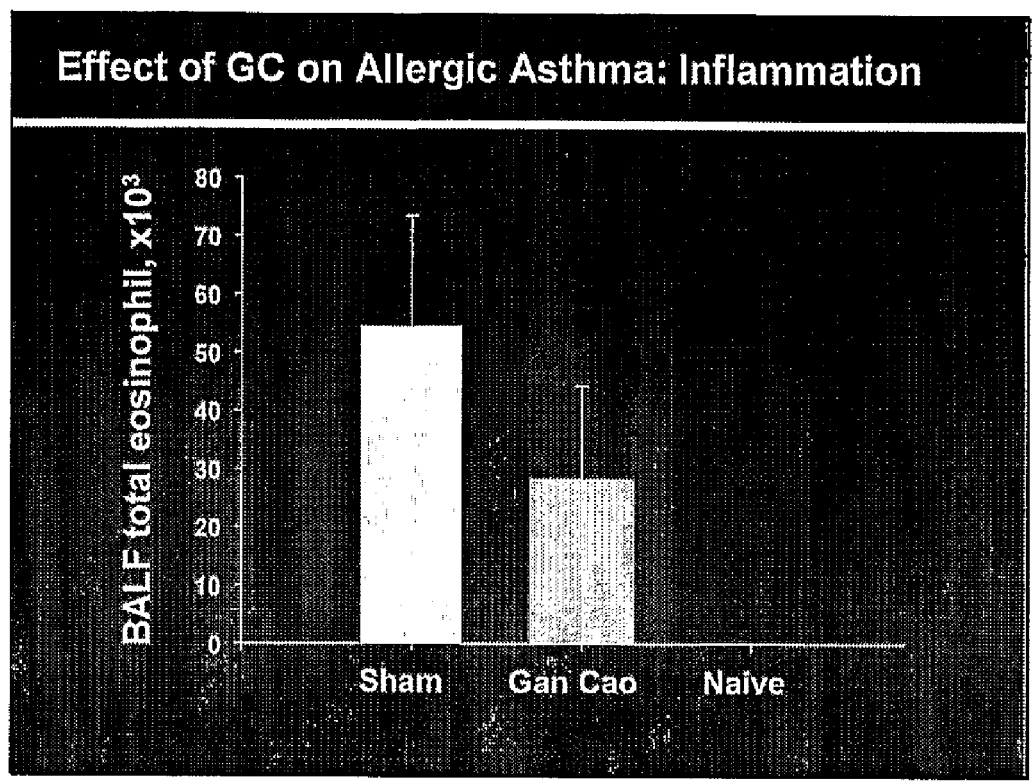
FIG. 36 shows the effect of Gan-Cao on eosinophil inflammation.

Effect of Gan-Cao on Eosinophil Inflammation: Results were obtained by methods substantially similar to those described herein and are set forth in FIG. 36.

Figure 37:
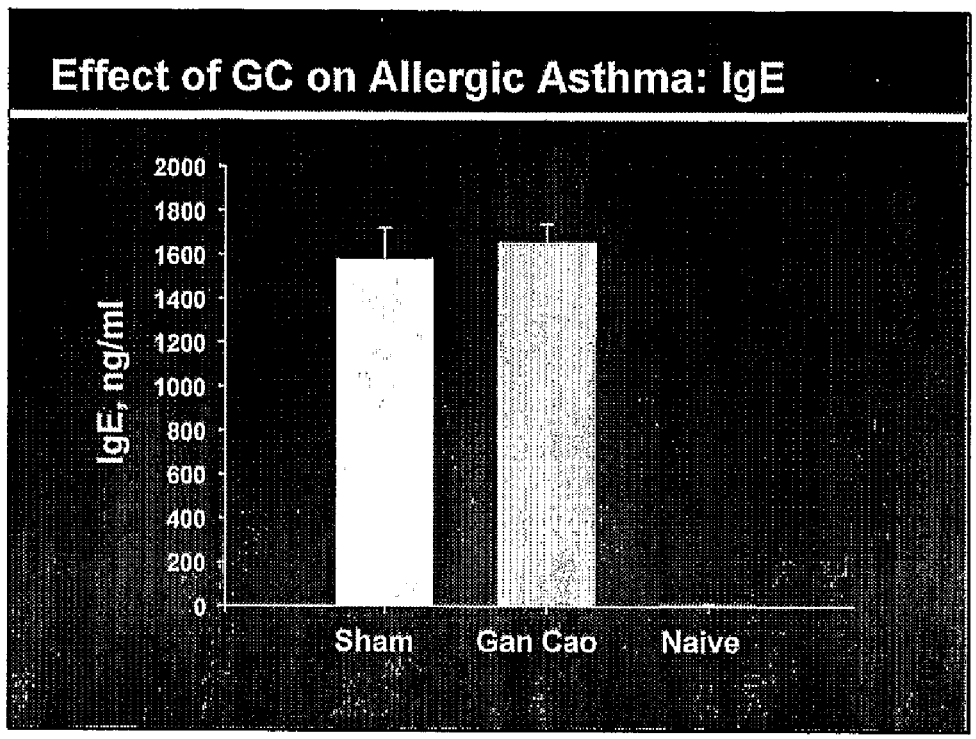
FIG. 37 shows the effect of Gan-Cao on IgE.

Effect of Gan-Cao on IgE: Results were obtained by methods substantially similar to those described herein and are set forth in FIG. 37.

Figure 38:
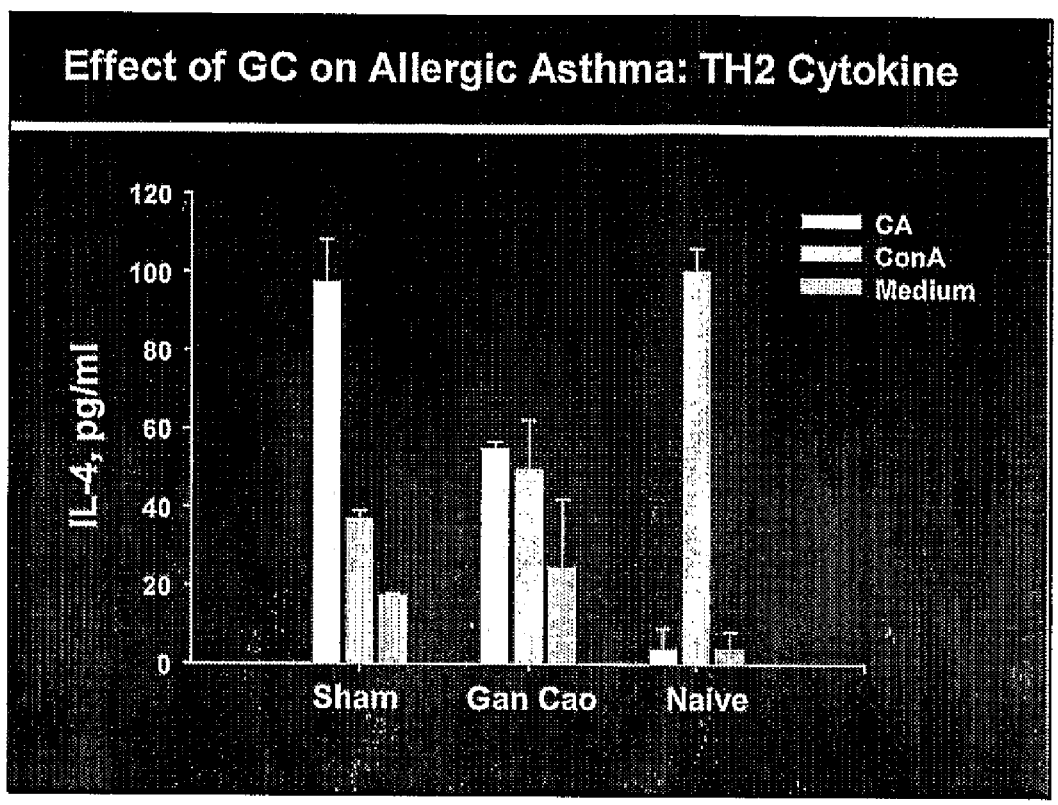
FIG. 38 shows the effect of Gan-Cao on Th2 cytokines.

Effect of Gan-Cao on Th2 Cytokines: Results were obtained by methods substantially similar to those described herein and are set forth in FIG. 38.

Figure 39:
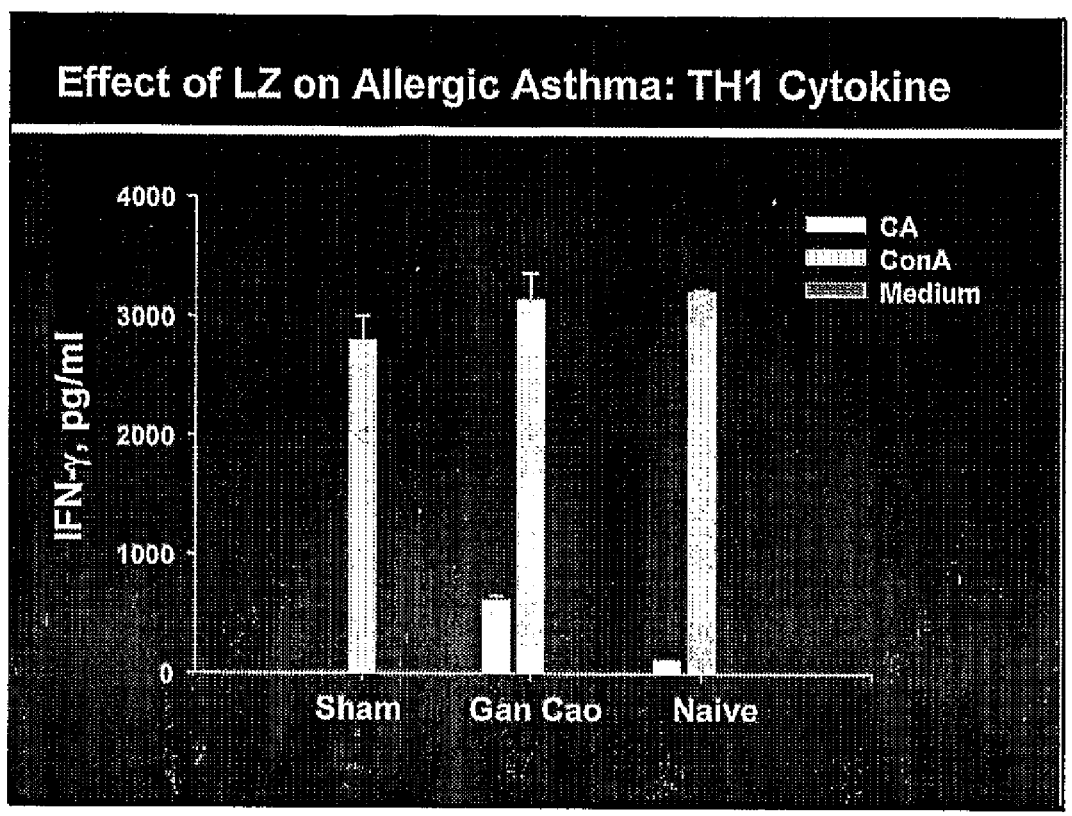
FIG. 39 shows the effect on Gan-Cao on Th1 cytokines.

Effect of Gan-Cao on Th1 Cytokines: Results were obtained by methods substantially similar to those described herein and are set forth in FIG. 39.

Effect of Gan-Cao on Kidney and Liver Function: Results were obtained by methods substantially similar to those described herein and are set forth in Table 10, below.

TABLE 10

Biochemical analysis of liver and kidney functions

|  | Sham | Gan-Cao | Naive | Reference Range |
|---|---|---|---|---|
| BUN | 19 ± 2 | 18 ± 1 | 21 ± 1 | 9-36 mg/dL |
| ALT | 55 ± 5 | 38 ± 3 | 33 ± 7 | 22-400 mg/dL |

Summary: Based on the extracts prepared in our laboratory, chromatographic fingerprints of ASHMI and its constituent individual herbs have been established using RP-HPLC/DAD. HPLC fingerprinting is an appropriate approach for standardization and quality control of ASHMI. Similar analytical procedure may be used to analyze the manufactured ASHMI product and the raw herbal material.

It is now well established that polarized T cell responses lead to the release of cytokines important in allergic responses. Th2 cells elaborate IL-4, IL-5, and IL-13 etc., but not IFN-γ. These Th2 cytokines promote IgE synthesis, eosinophil development and recruitment, and goblet cell hyperplasia, thus contributing to the allergic airway inflammation, and AHR. Studies have suggested that some anti-asthma traditional chinese medicine formulas may be able to reduce some asthma symptoms, perhaps reduction of allergic airway inflammation and AHR (Hsieh et al., Taiwan Asthma Study Group, Pediatr. Allergy Immunol. 7: 130, 1996; Egashira et al., Ann. NY. Acad. Sci. 685: 580, 1993; But et al., Clin. Rev. Allergy Immunol. 14: 253, 1996; Zhang et al., Chung. Kuo Chung. 17: 204, 1997; Xu et al., Chung. Kuo. Chung, 16: 198-200, 1996; Toda et al., Ann. N.Y. Acad. Sci. 685: 561-571, 1993; each of which is incorporated herein by reference). However, the mechanisms underlying these effects remain unclear.

Recent animal studies demonstrated that some traditional Chinese herbal formulations, such as TJ-19 (minor-blue-dragon), could decrease IgE (determined by PCA) responses by 43-910 (Recent Advances in the Pharmacology of KAMPO (JAPANESE HERBAL) MEDICINES. *Tokyo: Excerpta Medica*, 260: 1998; Hsieh et al., Taiwan Asthma Study Group, *Pediatr. Allergy Immunol.* 7: 130-140, 1996; Egashira et al., *Ann. NY Acad. Sci.* 685: 580, 1993; But et al., *Clin. Rev. Allergy Immunol.* 14:253, 1996; Zhang et al., Chung. Kuo Chung Hsi. I. Chieh. Ho. Tsa. Chih. 17:204, 1997; Xu et al., Chung. Kuo. Chung Hsi. I. Chieh. Ho. Tsa. Chih, 16:198, 1996; Toda et al., *Ann. N.Y. Acad. Sci.* 68 5: 561, 1993; each of which is incorporated herein by reference).

Those of ordinary skill in the art will readily appreciate that the foregoing has provided descriptions of certain embodiments of the present invention; various modifications and alterations to these descriptions can be made without departing from the spirit or scope of the present invention, which is defined as set forth in the following claims.

We claim:

1. An herbal formula for treating or lessening the severity of asthma, wherein said formula comprises an herbal mixture consisting of Ling-Zhi, Ku-Shen, and Gan-Cao, wherein:
    the ratio of Ling-Zhi to Ku-Shen is in the range of about 1:3 to about 27:1 Ling-Zhi:Ku-Shen;
    the ratio of Ling-Zhi to Gan-Cao is in the range of about 1:1 to about 53:1 Ling-Zhi:Gan-Cao; and
    the ratio of Ku-Shen to Gan-Cao is in the range of about 1:3 to about 18:1 Ku-Shen:Gan-Cao.

2. The herbal formula according to claim 1, wherein said herbal formula contains about 9 to 40 grams of Ling-Zhi.

3. The herbal formula according to claim 2, wherein said herbal formula contains about 3 to 15 grams of Ku-Shen.

4. The herbal formula according to claim 3, wherein said herbal formula contains about 1.5 to 9 grams of Gan-Cao.

5. A composition comprising the herbal formula according to claim 1 and a pharmaceutically acceptable carrier, adjuvant, or vehicle.

6. The composition according to claim 5, wherein said composition further comprises an additional therapeutic agent.

7. The composition according to claim 6, wherein said additional therapeutic agent is a corticosteroid.

8. The composition according to claim 7, wherein said corticosteroid is an inhaled corticosteroid.

9. The composition according to claim 6, wherein said additional therapeutic agent is a bronchodilator.

10. The composition according to claim 6, wherein said bronchodilator is an inhaled bronchodilator.

11. A method for treating or lessening the severity of asthma, in a patient in need thereof, wherein said method comprises administering to said patient the herbal formula according to claim 1.

12. The herbal formula according to claim 1, wherein the ratio of Ling-Zhi to Ku-Shen to Gan-Cao is in the range of about 6:2:1 to about 9:3:1 Ling-Zhi:Ku-Shen:Gan-Cao.

13. The herbal formula according to claim 1, wherein said herbal mixture consists of about 85% Ling-Zhi, about 8.5% Ku-Shen, and about 6.5% Gan-Cao.

* * * * *